United States Patent [19]
Senyei et al.

[11] Patent Number: 5,281,522
[45] Date of Patent: Jan. 25, 1994

[54] REAGENTS AND KITS FOR DETERMINATION OF FETAL FIBRONECTIN IN A VAGINAL SAMPLE

[75] Inventors: Andrew E. Senyei, San Juan Capistrano; Nelson N. H. Teng, Hillsborough, both of Calif.

[73] Assignee: Adeza Biomedical Corporation, Sunnyvale, Calif.

[21] Appl. No.: 628,282

[22] Filed: Dec. 14, 1990

Related U.S. Application Data

[63] Continuation-in-part of Ser. No. 274,268, Nov. 18, 1988, abandoned, and a continuation-in-part of Ser. No. 244,969, Sep. 15, 1988, Pat. No. 5,096,830, and a continuation-in-part of Ser. No. 274,267, Nov. 18, 1988, Pat. No. 5,223,440, and a continuation-in-part of Ser. No. 282,426, Dec. 12, 1988, Pat. No. 5,185,270.

[51] Int. Cl.$^5$ .................. C12Q 1/00; G01N 33/53; G01N 33/543
[52] U.S. Cl. ..................... 435/7.9; 436/518; 436/528; 436/536; 436/543; 436/547
[58] Field of Search .............. 436/547, 536, 518, 528, 436/543; 435/7.9

[56] References Cited

U.S. PATENT DOCUMENTS

| | | |
|---|---|---|
| 4,313,734 | 2/1982 | Leuvering . |
| 4,347,311 | 8/1982 | Schmitz .................. 435/810 |
| 4,353,982 | 10/1982 | Gomez et al. .............. 435/810 |
| 4,486,530 | 12/1984 | David et al. . |
| 4,632,901 | 12/1986 | Valkirs et al. . |
| 4,675,286 | 6/1987 | Calenoff . |
| 4,894,326 | 1/1990 | Matsuura et al. ............ 435/7.23 |

OTHER PUBLICATIONS

Boehringer Mannheim, "Antibodies and Reagents for Immunochemistry," *Biochemica*, pp. 129–134 (1989).
Wisdom, G.,. "Enzyme-Immunoassay," *Clin. Chem.*, pp. 1243–1255 (1976).
Gahl, et al, *Obstet. Gynecol.*, 60:297–304 (1982).
Grudzinskas, et al (ed.), *Pregnancy Proteins*, New York: Academic Press (1982).
Hess, et al, *Obstet. Gynecol.*, 68:25–28 (1986).
Huber, et al, *British J. Obstet. Gynecol.*, 90:1183–1185 (1983).
Konickx, et al, *British J. Obstet. Gynecol.*, 88:607–610 (1981).
Kuusela, et al, *Scand. J. Immunol.*, 12:331–337 (1980).
Matsuura, et al, *Proc. Natl Acad. Sci. USA*, 82:6517–6521 (1985).
Nakabayashi, et al, *Cancer Res.*, 42:3858–3863 (1982).
Oellerich, M., *J. Clin Chem. Clin. Biochem.*, 22:895–904 (1985).
Rochelson, et al, *Obstet. Gynecol.*, 69:163–165 (1987).
Ruoslahti, et al, *Int. J. Cancer*, 27:763–767 (1981).
Wisdom, G., *Clin. Chem.*, 22:1243–1255 (1976).

*Primary Examiner*—Sam Rosen
*Attorney, Agent, or Firm*—Skjerven, Morrill, MacPherson, Franklin & Friel

[57] ABSTRACT

This invention relates to methods, reagents and kits for detection of normal or ectopic pregnancy, the termination of pregnancy, or increased risk of preterm labor and rupture of membranes. Each embodiment involves sampling from the vaginal cavity, and determining the presence or absence of a specific analyte in the test sample. Sandwich or competition assay procedures can be used. Reagents and reagent kits for the above assays are included. The kit contains anti-(fetal fibronectin) antibody and an anti-fibronectin antibody.

46 Claims, No Drawings

REAGENTS AND KITS FOR DETERMINATION OF FETAL FIBRONECTIN IN A VAGINAL SAMPLE

CROSS REFERENCE TO RELATED APPLICATIONS

This application is a Continuation In Part of U.S. application Ser. No. 07/274,268, now abandoned, filed Nov. 18, 1988; U.S. application Ser. No. 07/244,969, now U.S. Pat. No. 5,096,830 filed Sep. 15, 1988; U.S. application Ser. No 7/274,267 filed Nov. 18, 1988 now U.S. Pat. No. 5,223,440; and U.S. application Ser. No. 07/282,426 filed Dec. 12, 1988 now U.S. Pat. No. 5,185,270. The inventors of the above-identified applications are ANDREW E. SENYEI and NELSON N. H. TENG. Each of those applications is incorporated herein by reference in its entirety.

FIELD OF THE INVENTION

This invention relates to reagents and kits for immunological detection of normal and ectopic pregnancy; the termination of pregnancy; and increased risk of preterm labor and rupture of membranes.

BACKGROUND OF THE INVENTION

A wide variety of tests have been developed for the determination of pregnancy. Commercial early pregnancy determinations generally involve assay of urine or serum. Home pregnancy tests for hCG (human chorionic gonadotropin) in urine include a variety of enzyme immunoassays, hemagglutination inhibition, and antibody-indicator agglutination tests which are effective to indicate pregnancy from 0 to 7 days after a missed period. Confirmation by physician is recommended, particularly to determine abnormal gestation such as ectopic pregnancy.

HCG is produced by the fetal trophoblast and passes from the fetal blood into the mother's blood through the intervillous space in the placenta. HCG levels in maternal blood and urine are often detectable at about 3 weeks. The sensitivity of serum or urine hCG tests is limited because the amount of hCG produced is determined by the amount of trophoblastic tissue, and by dilution of the hCG in the maternal fluids. Until development of the $\beta$-hCG specifically binding antibody, cross-reaction with LH (luteinizing hormone) also placed a limit on the level of sensitivity.

We have discovered that normal uterine pregnancies can be reliably determined early in the gestation cycle by testing a sample removed from the vicinity of the cervical canal, cervical os or posterior fornix of the vagina, preferably the external cervical os or posterior fornix, for the presence of fetal restricted antigens, that is, compounds or materials which are produced in the placental tissue and which do not pass in any substantial amounts into the maternal blood. Included in this class of antigens are fetal fibronectins.

We have discovered that ectopic pregnancy can be determined by testing a sample removed from the vicinity of the cervical canal or cervical os for the presence of fetal restricted antigens, that is, compounds or materials which are produced in the placental tissue and which do not pass in any substantial amounts into the maternal blood. Included in this class of materials are fetal fibronectins. If the fetal restricted antigens are substantially depressed in a sample from a person who is tested positive for pregnancy by a blood or urine test for pregnancy, an ectopic pregnancy is indicated.

Determination of the presence of ex vivo products of conception in uterine tissue removed in therapeutic or spontaneous abortion is critically important to confirm the existence of uterine pregnancy and the termination thereof, and to rule out the presence of an ectopic pregnancy. If levels of fetal associated antigens in maternal serum or urine indicate pregnancy, and the uterine tissue removed during a therapeutic abortion does not contain products of conception, a possible ectopic pregnancy is indicated. Presence of products of conception in uterine discharge associated with indicator of spontaneous abortion confirms the abortion, while the absence thereof indicates a continuation of pregnancy. Usual immunoassay techniques for determining the presence of fetal associated antigens in test samples derived from the vaginal cavity are not reliable for indicating the presence of products of conception since these samples typically contain maternal blood. Pregnancy antigens and fetal antigens are usually present in maternal blood as well as in fetal and placental tissue.

Determination of impending preterm births is critical for increasing neonatal survival of preterm infants. Detection of rupture of the amniotic membrane is important in distinguishing true and false labor. When the rupture is small and the volume of amniotic liquid escaping is small, the rupture is often undetected. Accepted methods for detecting ruptured membranes are subjective, not sufficiently sensitive, and not specific. An embodiment of this invention for detection of increased risk of preterm labor and rupture of the amniotic membrane after week 20 of pregnancy is directed to an assay of a test sample removed from the vicinity of the posterior fornix, cervical canal, or cervical os.

SUMMARY OF THE INVENTION

The method of this invention is used to determine the presence and/or status of a pregnancy. The method herein is used to determine the presence of a diagnostic indicator in a sample derived from the vaginal cavity, and comprises:

(a) a method for determining normal uterine pregnancy during the first 20 weeks of pregnancy comprising obtaining a test sample in the vicinity of the cervical canal or cervical os, and determining the presence of a fetal restricted antigen in the sample;

(b) a method for determining fallopian pregnancy comprising obtaining a test sample in the vicinity of the cervical canal or cervical os from a pregnant patient during the first 20 weeks of pregnancy, and determining the absence of a fetal restricted antigen in the sample;

(c) a method for determining ex vivo products of conception comprising obtaining a test sample expelled or removed from the uterus, and determining the presence of a fetal restricted antigen in the sample; or (d) a method for determining increased risk of preterm labor or fetal membrane rupture comprising obtaining a test sample in the vicinity of the posterior fornix, cervical canal or cervical os, from a patient after week 20 of pregnancy, and determining the presence of a fetal restricted antigen in the sample.

Reagents for use with the assays of the invention include labeled and unlabeled anti-(analyte) antibodies, i.e., anti-(fetal restricted antigen) antibodies such as anti-(fetal fibronectin) antibodies; anti-(analyte class) antibodies, i.e., anti-(fetal restricted antigen class) antibodies such as anti-(fibronectin) antibodies, and the like.

Other reagents for use with the assays of the invention include insoluble supports to which are adhered the anti-(analyte) antibodies, i.e., anti-(fetal restricted antigen) antibodies such as anti-(fetal fibronectin) antibodies; anti-(analyte class) antibodies, i.e., anti-(fetal restricted antigen class) antibodies such as anti-(fibronectin) antibodies, and the like. Labeled or unlabeled reagent fetal restricted antigens are also reagents of this invention. Reagents for use with the assays of this invention also include insoluble supports to which are adhered reagent analyte, i.e., insoluble supports to which are adhered fetal restricted antigens. Reagents for use with the assays also include immunoassay reagents such as labeled secondary antibody, positive and negative controls, label development reagents such as enzyme substrate, and wash buffer.

This invention includes kits comprising one of the above reagents, alone, in combination with another reagent or in combination with supplies such as sample preparation devices. The reagents can be present in any suitable form in the kit, for example in containers, packages, and the like.

DETAILED DESCRIPTION OF THE INVENTION

The method of this invention for determining the presence and/or status of a pregnancy comprises determining the presence of a fetal restricted antigen, in a test sample removed from the vaginal cavity in the vicinity of the posterior fornix, cervical canal, or cervical os, and especially at the cervical canal or cervical os. Specific embodiments of this invention are used to determine normal uterine pregnancy, ectopic pregnancy, the occurrence of a therapeutic or spontaneous abortion, and increased risk of preterm labor or rupture of the membranes.

Reagents and kits useful in performing the method are also described.

FETAL RESTRICTED ANTIGEN TEST METHODS AND REAGENTS

A fetal restricted antigen testing method involves the detection of a fetal restricted antigen, that is, a uniquely fetal or placental focused material, in a test sample removed in the vicinity of the posterior fornix, cervical canal or cervical os. We have discovered that detectable amounts of these materials are present in such a sample. Since the fetal restricted antigens are not present in significant quantities in the maternal blood, the presence of maternal blood in the sample does not interfere with the test.

The term "fetal restricted antigen" as used herein is defined to mean a uniquely fetal or placental derived material, which is either not present in maternal serum, plasma or urine, or is not present in significant amounts in maternal serum, plasma or urine. Any substance meeting this definition is intended to be included within the meaning of the term, including both immunogenic materials and proteins and other substances which are not immunogenic in their purified form but which have unique epitopes which can be selectively bound with antibodies specific or selective thereto. An example of a fetal restricted antigen is the fetal fibronectin which binds specifically with the FDC-6 monoclonal antibody described by H. Matsuura and S. Hakomori, *Proc. Natl. Acad. Sci. USA* 82:6517–6521 (1985). Production of the hybridoma (deposited at the American Type Culture Collection as accession number ATCC HB 9018) which produces FDC-6 antibody is also described in detail in U.S. Pat. No. 4,894,326 issued Jan. 16, 1990 to Matsuura et al.

The term "fetal restricted antigen class" as used herein is defined to mean a class or group of antigens of which the fetal restricted antigen is a member. For example, fetal fibronectin is a fetal restricted member of the human fibronectin group or class.

The term "antibody" as used herein is defined to include antibodies of classes IgG, IgM, IgA, IgD, and IgE, and preferentially binding fragments and hybrid derivatives of antibodies, including Fab and F(ab')$_2$ fragments of antibodies. Antibodies may be polyclonal or monoclonal. Generally, monoclonal antibodies are preferred for use in the assays of this invention.

Immunological methods are most convenient for carrying out the assays of this invention because of their specificity, and the term "immunoassays" as used herein is defined to mean any method using a preferential binding of an antigen with a second material (i.e., a binding partner, usually an antibody or antibody fragment having an antigen binding site) which binds preferentially with an epitope of the antigen. Preferential binding as used herein refers to binding between binding partners which is selective and generally specific, and which demonstrates generally less than 10%, preferably less than 5%, cross-reactive nonspecific binding. For example, when the analyte is fetal fibronectin, the anti-(fetal fibronectin) antibody is less than 10%, and preferably less than 5%, cross-reactive with adult fibronectins.

Included within the scope of this invention are all immunoassays including this step, including but not limited to sandwich, competition, dip stick, agglomeration, precipitation, transistor bridge probe, particle sorting, light disturbing, light scattering, and ultrasonic probe immunoassays, for example. Appropriate immunoassays may use radioisotopes, enzymes, or fluorogenic, chromogenic, or chemiluminescent substances, for example, as labels.

A test sample which is to be assayed is removed in the vicinity of posterior fornix, the cervical canal or cervical os, and the sample is assayed to determine the presence or quantity of fetal restricted antigen in the sample. Preferably, the presence of the antigen is determined. The sample generally comprises fluid and particulate solids, and may contain vaginal or cervical mucus, other vaginal or cervical secretions, cells or cell debris, amniotic fluid, or other fetal or maternal materials. The sample is removed with a swab having a dacron or other fibrous tip, aspirator, suction device, lavage device or the like and is transferred to a suitable container for storage and transport to the testing laboratory.

It is important that the test sample be dispersed in a liquid which preserves the sensitive protein analytes which are unstable in the sampled composition. The storage and transfer medium should prevent decline in the protein analyte level during storage and transport. A suitable preserving solution for storage and transfer consists of 0.05M Tris-HCl, pH 7.4; 0.15M NaCl, 0.02% NaN$_3$, 1% BSA, 500 Kallikrein Units/mL of aprotinin, 1 mM phenylmethylsulfonyl fluoride (PMSF) and 5 mM EDTA, and is described in U.S. Pat. No. 4,919,889, issued Apr. 24, 1990. The solution is the most preferred sample diluent solution when detecting fetal fibronectin.

Detection of fetal restricted antigen can be achieved by binding the fetal restricted antigen in a test sample with an antibody which binds preferentially with an epitope of the fetal restricted antigen, and determining the presence or absence of this binding.

In one sandwich assay for fetal restricted antigen, the test sample is contacted with an insoluble support to which anti-(fetal restricted antigen) antibody is adhered to effect binding of fetal restricted antigen in the sample to the insoluble support. The insoluble support is then contacted with a secondary antibody, an unlabeled or labeled anti-(fetal restricted antigen) antibody, which binds with the fetal restricted antigen adhering to the insoluble support to detect and measure the captured fetal restricted antigen.

An antibody which binds with a class of substances including the analyte fetal restricted antigen can be substituted for a specific anti-(fetal restricted antigen) antibody capture antibody or the specific anti-(fetal restricted antigen) antibody sandwiching antibody. For example, anti-(fetal fibronectin) antibody can be adhered to the insoluble support, and labeled or unlabeled anti-(fibronectin) antibody can be used to detect the captured antigen. Alternatively, anti-(fibronectin) antibody can be adhered to the insoluble support, and labeled or unlabeled anti-(fetal fibronectin) antibody is used to label the captured antigen. Preferably, the anti-(fetal restricted antigen) antibody is used as the capture antibody to ensure detection when the fetal restricted antigen is present in small amounts in the sample in comparison to other antigens of the class.

The secondary antibody can have a physically detectable label which can be measured directly on the insoluble support. Alternatively, the secondary antibody can be unlabeled, and the secondary antibody can be determined by contacting the insoluble support with a labeled antibody or antibody fragment which binds selectively with the secondary antibody (i.e., a tertiary antibody), removing unbound labeled tertiary antibody from the support, and determining the presence of the label on the insoluble support. Sandwich immunoassays using a membrane substrate are appropriate for use.

The sample can also be tested by a competition immunoassay procedure. The test sample is mixed with labeled reagent antibody or antigen and incubated with an insoluble support to which an anti-(fetal restricted antigen) antibody or reagent fetal restricted antigen is adhered, competition occurring between the reagents for binding with the sample analyte. Methods and procedures to accomplish such immunoassays are well known to those skilled in the immunoassay art. The label ultimately adhering to the insoluble support or remaining in the solution is determined.

Anti-(fetal restricted antigen) antibody can be obtained from fetal restricted antigens, preferably from highly purified fetal restricted antigens, by conventional antiserum or monoclonal techniques. This invention will be described herein with respect to the detection of fetal fibronectin as a fetal restricted antigen, for purposes of clarity, and not by way of limitation: the detection of any fetal restricted antigen is intended to be within the scope of this invention. Fetal fibronectin is purified from amniotic fluid as described by Engvall and Ruoslahti, *Int. J. Cancer* 20:1-5 (1977). Anti-(fetal fibronectin) antibody can be derived from fetal fibronectin by conventional antiserum techniques or by monoclonal antibody techniques.

Both monoclonal and polyclonal anti-(fetal restricted antigen) antibodies, or anti-(fetal restricted antigen class) antibodies can be derived directly from fetal restricted antigens, preferably from highly purified antigens, by conventional antiserum or monoclonal techniques.

The principal antibodies useful in the assays of this invention are IgG and IgM antibodies, although the IgD, IgE and IgA antibodies can also be used if available in sufficient quantity. The antibodies are then affinity purified using conventional affinity chromatography techniques such as those described by Mishell and Shiigi in SELECTED METHODS IN CELLULAR IMMUNOLOGY. San Francisco: Freeman (1980), Goding, J., MONOCLONAL ANTIBODIES: PRINCIPLES AND PRACTICE. New York: Academic Press pp 111-114 (1983), and Parikh et al, C&EN (Aug. 26, 1985).

Preferentially binding antibody fragments suitable for use in the kit and method of this invention can be made from the respective monoclonal or polyclonal antibodies by conventional enzyme or chemical fragmentation procedures. Suitable procedures are described by Tijssen, P. LABORATORY TECHNIQUES IN BIOCHEMISTRY AND MOLECULAR BIOLOGY: PRACTICE AND THEORIES OF ENZYME IMMUNOASSAYS. New York: Elsevier (1985), for example.

Polyclonal anti-(fetal restricted antigen) antibody can be obtained by immunizing an animal such as a rabbit, guinea pig, rat or goat with concentrated fetal restricted antigen, such as fetal fibronectin, removing serum from the immunized animal, and separating the immunoglobulins from the serum, for example by ammonium sulfate precipitation.

Suitable absorbents for use in affinity chromatography include cross-linked agarose and cross-linked polyacrylamides to which the fetal restricted antigen antibody is covalently bonded. For removal of antibodies cross-reacting with adult fibronectins, the antibody serum is passed through columns to which are coupled adult fibronectins. A portion of the eluant containing the remaining antibody can then be passed through a fetal fibronectin column and eluted to yield the affinity purified antibody.

In these procedures, the antibody solution can be applied to the column in a phosphate buffered saline solution, and the antibodies can be eluted with a 2.5M NaSCN solution, pH 8.0. Antibody concentration, if desired, can be achieved by negative pressure dialysis or ultrafiltration. The antibody solution is stable at temperature of 4° C. or less. Repetition of the column separation procedures is continued until the desired separation and purity is achieved.

For production of fetal fibronectin antigen and antibodies the procedures described by H. Matsuura and S. Hakomori, *Proc. Natl. Acad. Sci. USA* 82:6517-6521 (1985) can be followed, replacing the tumor fibronectin with fetal fibronectin. A most preferred anti-(fetal fibronectin) antibody is produced by the hybridoma deposited at the American Type Culture Collection and given the accession number ATCC HB 9018 is described in detail in U.S. Pat. No. 4,894,326 issued Jan. 16, 1990 to Matsuura et al. That monoclonal antibody is designated FDC-6. Culture of the hybridoma and preparation of the antibodies for use in an immunoassay is described in detail in the Examples.

Anti-(fetal restricted antigen class) antibodies of both polyclonal and monoclonal varieties are generally well known and available either commercially or from publicly available hybridoma deposits. For example, anti-(fibronectin) monoclonal antibodies can be derived from clone samples from ATCC HB 91 (American Type Culture Collection, Rockville, Md.). Other such antibodies are described in Japanese Patent Application 60091264 (DIALOG database file 351, WPI Acc. No. 85-161617/27) and U.S. Pat. No. 4,325,867. A preferred procedure for preparation of polyclonal anti-fibronectin antibodies in goats and rabbits is described in the Examples.

Sandwich Immunoassays: In a sandwich embodiment of this invention to determine fetal restricted antigen in a test sample, an insoluble support to which anti-(fetal restricted antigen) antibody is adhered is contacted with a test sample diluted with an aqueous buffer solution for a sufficient time to permit binding of fetal restricted antigen in the test sample with the anti-(fetal restricted antigen) antibody on the insoluble support, and then removing the sample from the support. Suitable immunoassay solutions are well known and include buffer solutions such as phosphate buffer solution (PBS), pH 6 to 8 and preferably from 7.2 to 7.6. Preferably, the sample is diluted in the sample diluent solution described hereinbefore. The incubation time should be sufficient to permit substantial binding to occur, the time being temperature dependent. Suitable incubation times are from 30 to 240 minutes at temperatures within the range of from 16° to 40° C., the preferred contact time being at least 60 minutes at temperatures within the range of from 20° to 26° C.

Residual sample solution is then removed from the support by use of a rinse solution. Any conventional rinse solution can be used. A suitable rinse solution is described in U.S. Pat. No. 4,528,267. It is an aqueous phosphate buffer solution having a phosphate molarity of from 0.0001 to 0.05, a pH of from 6 to 8 and containing from 0.001 to 0.1 weight percent of nonionic surfactant. Suitable nonionic surfactants include polyoxyethylene ethers (BRIJ such as lauryl, cetyl, oleyl, stearyl, and tridecyl polyoxyethylene ethers; polyoxyethylene sorbitans (TWEEN such as polyoxyethylene sorbital monolaurate, monopalmitate, monostearate, monoleate, and trioleates); and other polyoxyethylene ethers (TRITON, for example). Preferred nonionic surfactants are octylphenoxypolyethoxy ethanol having 40 ethylene oxide units (TRITON X-405, Rohm and Hass Company) and polyoxyethylene sorbital monolaurate (TWEEN 20, available commercially from Sigma Chemical Company). A most preferred rinse solution is 0.02M Tris, 0.08M sodium chloride, 0.05% Tween-20, and 0.02% sodium azide.

The insoluble support is then contacted with an antibody which will bind with the captured fetal restricted antigen on the insoluble support, i.e., the sandwiching antibody. The sandwiching antibody can be an anti-(fetal restricted antigen) antibody, or can be an anti-(fetal restricted antigen class) antibody. The sandwiching antibody can be labeled or unlabeled. In the event that an unlabele sandwiching antibody is used, a tertiary antibody which binds with the sandwiching antibody and which bears a physically detectable label can be used in a conventional manner to determine the sandwiching antibody.

A variety of labels are described herein. For purposes of clarity and not by way of limitation, the subsequent steps of the process will be described for anti-(fetal restricted antigen) antibodies which have been labeled with an enzyme, preferably a chromogenic or a fluorogenic enzyme. The term "chromogenic enzyme" is defined herein to refer to an enzyme which will produce a chromophore product with a suitable substrate. The term "fluorogenic enzyme" is defined herein to refer to an enzyme which will produce a fluorophore product with a suitable substrate.

The sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. A preferred diluent for an enzyme-conjugated antibody is 0.05M Tris Buffer pH 7.2, 2% D-Sorbitol, 2% BSA, 0.1% Sodium Azide, 0.01% Tween-20, 1 mM Magnesium Chloride, and 0.1% Zinc Chloride.

The incubation is continued for sufficient time to permit the sandwiching antibody to bind with exposed fetal restricted antigen epitopes, if any, adhering to the insoluble support. The preferred incubation times and temperatures are as set forth above for the binding of insolubilized reagent anti-(fetal restricted antigen) antibody with the test sample fetal restricted antigen.

The sandwiching antibody solution is then removed from the insoluble support, and the support is rinsed with a rinse solution such as described above, to remove any residual, unbound material.

If the sandwiching antibody is unlabeled, an enzyme labeled antibody or other binding agent which binds selectively with the sandwiching antibody is applied to the insoluble support in an aqueous solution. The solution preferably contains suitable salts and buffers to preserve the reactants and facilitate the binding reaction, such as described above. The incubation is continued for sufficient time to permit labeled anti-(sandwiching antibody) antibody to bind with exposed sandwiching antibody epitopes, if any, adhering to the insoluble support. The preferred incubation times and temperatures are as set forth for the binding of insolubilized reagent anti-(fetal restricted antigen) antibody with the test sample fetal restricted antigen.

The labeled antibody solution is then removed from the insoluble support, and the support is rinsed with a rinse solution such as described above, to remove any residual, unbound labeled material.

In a next step, the insoluble support is contacted with an aqueous solution of a substrate which undergoes a reaction in the presence of the enzyme to release fluorescent or chromogen compound into the solution. Suitable substrates and the enzymes with which they can be converted are described in U.S. Pat. Nos. 4,190,496 and 4,528,267, for example. The support is contacted with an aqueous solution of the substrate containing from $10^{-2}$ to $10^{-10}$ molar concentrations of the substrate. Substrate molar concentrations of from $10^{-4}$ to $10^{-5}$ are preferred. Preferred additional reagents and buffers in the substrate solution include 2-amino-2-methyl-1-propanol buffer and magnesium chloride, for example.

The substrate solution is incubated with the insoluble support for sufficient time for the reaction yielding the fluorophore or chromophore to occur. At temperatures of from 18° to 40° C., incubation times of from 5 to 240 minutes can be used. Preferably, the temperature is within the range of from 20° to 26° C., and the incubation time is from 10 to 90 minutes.

The fluorescent or chromophore level in the solution is then measured. The equipment and procedures for determining the level of fluorescence or chromophore level in the substrate solutions are those conventionally used in the art. The level of fluorescence or chromogen in solution is a function of the enzyme concentration on the insoluble support which is, in turn, a function of the amount of fetal restricted antigen in the test sample. The concentration of the fetal restricted antigen can be determined by comparing the fluorescence or chromophore level of the solution with respective fluorescence or chromophore levels obtained with control solutions containing known concentrations of fetal restricted antigen. Preferably, a control having a concentration of the fetal restricted antigen which is statistically significantly different from background is used. For fetal fibronectin, the control can be amniotic fluid having a known fetal fibronectin concentration. The amniotic fluid can be purified prior to use, if desired. The fetal fibronectin concentration can vary from about 1 to about 1,000 ng/mL, preferably from about 10 to 100 ng/mL, most preferably about 50 ng/mL. Samples having an absorbance greater than or equal to that of the control are considered positive. A preferred sandwich assay is described in detail in the Examples.

The sandwich procedure can be modified to use a fetal restricted antigen class binding antibody as either the capture or, preferably, the sandwiching antibody. In these embodiments, an anti-(fetal restricted antigen class) antibody, such as an anti-(fibronectin) antibody, is adhered to the insoluble support, and a labeled or unlabeled anti-(fetal restricted antigen) antibody is applied as the sandwiching antibody. Preferably, the anti-(fetal restricted antigen) antibody can be adhered to the insoluble support, and a labeled or unlabeled anti-(fetal restricted antigen class) antibody is used to sandwich the captured antigen.

Membrane Immunoassays: In a membrane embodiment of this invention to determine fetal restricted antigen in a test sample, an insoluble support to which anti-(fetal restricted antigen) antibody is adhered is contacted with a test sample diluted with an aqueous buffer solution such as phosphate buffer solution (PBS), pH 6 to 8 and preferably from 7.2 to 7.6, for a sufficient time to permit binding of fetal restricted antigen in the sample with the anti-(fetal restricted antigen) antibody on the insoluble support. The time required for binding is very small in a flow through system. Suitable incubation times can be one second up to 20 minutes at temperatures within the range of from 16° to 40° C., the preferred contact time being less than one minute and optimally from 10 seconds to 2 minutes.

The insoluble support is then contacted with an antibody which will bind with the captured fetal restricted antigen on the insoluble support, i.e., the sandwiching antibody. The sandwiching antibody can be labeled or unlabeled. In the event that an unlabeled sandwiching antibody is used, a tertiary antibody which binds with the sandwiching antibody and which bears a physically detectable label can be used in a conventional manner to determine the sandwiching antibody.

A variety of labels are described herein. For purposes of clarity and not by way of limitation, the subsequent steps of the process will be described for anti-(fetal restricted antigen) antibodies which have been labeled with an enzyme, preferably a fluorogenic or chromogenic enzyme.

The sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit the sandwiching antibody to bind with exposed fetal restricted antigen epitopes, if any, adhering to the insoluble support. The preferred incubation times and temperatures are as set forth for the binding of insolubilized reagent anti-(fetal restricted antigen) antibody with the test sample fetal restricted antigen.

The sandwiching antibody solution optionally can be removed from the insoluble support, and the support is rinsed with a rinse solution such as described above, to remove any residual, unbound labeled material.

If the sandwiching antibody is unlabeled, an enzyme labeled antibody or other binding agent which binds selectively with the sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit labeled anti-(sandwiching antibody) antibody to bind with sandwiching antibody epitopes, if any, adhering to the insoluble support. The preferred incubation times and temperatures are as set forth for the binding of insolubilized reagent anti-(fetal restricted antigen) antibody with the test sample fetal restricted antigen.

The labeled antibody solution is then removed from the insoluble support, and the support is rinsed with a rinse solution such as described above, to remove any residual, unbound labeled material.

In a next step of the membrane sandwich process of this invention, the insoluble support is contacted with an aqueous solution of a substrate which undergoes a reaction in the presence of the enzyme to release fluorogen or chromogen compound into the solution. Suitable substrates and the enzymes with which they can be converted, as well as additional components and buffers have been described above.

The substrate solution is incubated with the insoluble support for sufficient time for the reaction yielding the fluorophore or chromophore to occur. At temperatures of from 18° to 40° C., incubation times of from 1 to 20 minutes can be used. Preferably, the temperature is within the range of from 20° to 26° C., and the incubation time is from 2 to 5 minutes. The fluorogen or chromogen level on the membrane can be measured using a reflectometer or densitometer.

In an alternate membrane embodiment, an anti-(fetal restricted antigen) antibody is bound to the membrane. The sample and a labeled anti-(fetal restricted antigen class) antibody are combined. Following a time sufficient for antibody binding, the sample/conjugate solution is contacted with the membrane. Fetal restricted antigen in the sample binds to the anti-(fetal restricted antigen) antibody, producing a sandwich of anti-(fetal restricted antigen) antibody/fetal restricted antigen/labeled anti-(fetal restricted antigen class) antibody on the membrane. In a preferred embodiment, the label is colloidal gold.

Competition Immunoassays: Competition embodiments of this invention using labeled reagent fetal restricted antigen comprise contacting a mixture of the test sample and the labeled reagent fetal restricted antigen with an anti-(fetal restricted antigen) antibody adhered to an insoluble support, and determining the amount of label which either binds with the insoluble support or remains in the solution phase.

The competition embodiments of this invention using labeled anti-(fetal restricted antigen) antibodies can be of more than one form. One embodiment using anti-(fetal restricted antigen) antibody bound to the insoluble support comprises contacting a mixture of the test sample and labeled anti-(fetal restricted antigen) antibodies with an anti-(fetal restricted antigen) antibody adhered to an insoluble support, and determining the amount of label which either binds with the insoluble support or remains in the solution phase. Another embodiment using reagent fetal restricted antigen bound to the insoluble support comprises contacting a mixture of the test sample and labeled anti-(fetal restricted antigen) antibodies with a fetal restricted antigen adhered to an insoluble support, and determining the amount of label which either binds with the insoluble support or remains in the solution phase.

In each of these methods, the test sample is diluted with buffer solution, incubated and the label determined as described above with respect to the sandwich immunoassay embodiments. The concentration of the limiting reagent is selected to permit competitive binding between the reagents, with the amount of label remaining on the insoluble support or in the solution being a variable which is a function of the amount of the analyte in the test sample. These methods are generally well known and how to vary them to optimize a procedure are fully within the knowledge of a person skilled in the immunoassay art.

The binding of the anti-(fetal restricted antigen) antibody and the fetal restricted antigen in the test sample can also be determined by agglomeration of particles to which the anti-(fetal restricted antigen) antibody is adhered by fetal restricted antigen in the sample, precipitation of antibodies due to antibody-antigen reactions, or observations of physical or electrical changes which occur upon the antibody-antigen binding, using semiconductor bridge probes, light disturbing patterns such as are described in U.S. Pat. No. 4,647,544, and the like.

Fetal Restricted Antigen Test Kits for determining fetal restricted antigen in a test sample included within the scope of this invention generally include an anti-(fetal restricted antigen) antibody adhered to an insoluble support and an anti-(fetal restricted antigen class) antibody. In a preferred embodiment the anti-(fetal restricted antigen) antibody is a monoclonal antibody and the anti-(fetal restricted antigen class) antibody is a polyclonal antibody. More preferably, the anti-(fetal restricted antigen class) antibody is labeled with an enzyme, preferably alkaline phosphatase. The kit can additionally contain enzyme substrate, a positive control, a negative control, rinse buffer, or one or more sample preparation devices such as sample filtering devices.

The kits of this invention can further comprise combinations to determine a fetal restricted antigen in a test sample; buffers for sample transport, storage and dilution; vials, foil packages or other containers of reagents of this invention; other, optional reagents such as enzyme substrate reagents in separate vials or other packages; mechanical or optical devices to determine the presence and extent of antibody-antigen binding; and combinations thereof. Sampling devices such as sampling swabs, and buffers for transport and storage can also be included or packaged separately. The individual parts of the kit may be packaged in any convenient form, such as vials, foil packages, or other containers. For example, insoluble support structures in a foil package can be combined with other reagents in vials or other packages. A most preferred container for the liquid reagents in the kit is a polyethylene dropper bottle container which accurately dispenses an appropriate size drop; e.g. 50 or 100 µL. A preferred kit is described in detail in the Examples.

FETAL RESTRICTED ANTIGEN PREGNANCY TEST

A pregnancy testing embodiment involves the detection of a fetal restricted antigen, that is, a uniquely fetal or placental focused material, in a test sample removed in the vicinity of the cervical canal or cervical os. We have discovered that detectable amounts of these materials are present in such a sample during the first 20 weeks of pregnancy. Since the fetal restricted antigens are not present in significant quantities in the maternal blood, the presence of maternal blood in the sample does not interfere with the test.

The assay is performed as described above. A determination of the presence of fetal restricted antigen in the test sample indicates pregnancy.

ECTOPIC PREGNANCY TEST

A method of this invention which determines ectopic pregnancy involves the detection of the presence or absence of a fetal restricted antigen in a test sample removed in the vicinity of the cervical canal and/or cervical os. Detectable amounts of these materials are normally present in such samples during the first 20 weeks of normal pregnancy. The absence of fetal restricted antigen in such a sample from a pregnant woman during the first 20 weeks of pregnancy is indicative of the presence of an ectopic pregnancy. Since the fetal restricted antigens are not present in significant quantities in the maternal blood, the presence of maternal blood in the sample does not interfere with the test.

A test sample which is to be assayed is removed in the vicinity of the cervical canal and/or cervical os, and the sample is assayed to determine the presence or quantity of fetal restricted antigen in the sample as described. It may also be desirable to determine pregnancy using the presence of pregnancy-indicating hormones in serum or urine. A wide variety of methods are known to a person skilled in the art for determining pregnancy using the blood or urine of a patient. Any reliable method can be used. Procedures for measuring hCG in plasma, serum and/or urine are described in U.S. Pat. Nos. 3,171,783, 3,234,096, 3,236,732, 3,298,787, 3,309,275, 3,485,751, 3,655,838, 3,689,633, 3,862,302, 3,873,682, 3,873,683, 3,833,304, 3,991,175, 4,003,988, 4,014,653, 4,016,250, 4,033,723, 4,071,314, 4,094,963, 4,123,224, 4,123,509; 4,138,214, 4,208,187, 4,210,723, 4,234,561, 4,256,629, 4,268,435, 4,270,923, 4,310,455, 4,313,871, 4,320,111, 4,348,207, 4,371,515, 4,419,453, 4,421,896, 4,493,793, 4,508,829, and 4,665,034, for example. Pregnancy detection by measuring progesterone metabolites in urine (U.S. Pat. No. 3,141,740) or in milk, serum or plasma (Hungary Patent No. T37028, WPI No. 86-023344/04); human placental lactogen in serum or plasma (U.S. Pat. Nos. 3,892,841, 4,371,515, and 4,493,793); estrogen steroids in urine (U.S. Pat. No. 3,955,928); luteinizing hormone (LH), prolactin (PRL) and/or hCG-like substances in serum, plasma or urine (U.S. Pat. Nos. 4,016,250, 4,094,963, and 4,320,111); pregnancy specific $\beta_1$-glycoprotein (U.S. Pat. Nos. 4,065,445 and 4,191,533); LH (U.S. Pat. Nos. 4,138,214 and 4,208,187); bovine pregnancy antigen in bovine serum or urine (European Patent Application 188,551, WPI No. 86-042108/06); a new placental protein (U.S. Pat. No. 4,592,863); and early pregnancy factor WO 8605498 (WPI No. 86-264940/40) have been described. Methods have been described for determining pregnancy by adding dyes to urine (U.S. Pat. Nos. 2,587,221 and 3,226,196, dinitrophenylhydrazine; U.S. Pat. No. 3,595,620, bromocresol purple or chlorophenol red), by an iodine-paper test (U.S. Pat. No. 3,248,173), by adding other precipitating agents (U.S. Pat. No. 3,278,270), by a treatment of female blood with a mixture of acids and sodium chloride (U.S. Pat. No. 3,883,304). Pregnancy may be determined using an assay of a test sample removed in the vicinity of the cervical canal or cervical os following the teachings of U.S. application Ser. No. 121,902 filed Nov. 17, 1987. Any one of the above methods can be used, but methods such as hCG measurements are preferred.

A determination of the presence of pregnancy together with a negative determination of fetal restricted antigen in the test sample during the first 20 weeks of pregnancy indicates the absence of normal uterine pregnancy, and is an indication that an ectopic pregnancy has occurred.

EX VIVO PRODUCTS OF CONCEPTION TEST

An embodiment of this invention which determines the presence of ex vivo products of conception involves the detection of a fetal restricted antigen in a test sample expelled by a suspected spontaneous abortion or removed during a dilation and curettage or a therapeutic abortion procedure. Since the fetal restricted antigens are not present in significant quantities in maternal blood, the presence of maternal blood in the sample does not interfere with the tests.

A test sample which is to be assayed for the presence of ex vivo products of conception is procured which is believed to represent material expulsed from the uterus. Such materials can be tissues removed during a therapeutic abortion or a D&C (dilation and curettage). Alternatively, the material may be vaginal discharge which is believed to be indicative of a spontaneous abortion, or miscarriage. The sample generally comprises fluid and particulate solids, and may contain tissue matter, vaginal or cervical mucus, other vaginal or cervical secretions, cells or cell debris, amniotic fluid, or other fetal or maternal materials. The sample can be procured from the vaginal cavity with a swab having a dacron or other fibrous tip, aspirator, suction device, lavage device or the like. The sample can represent tissues removed during a dilation and curettage procedure or a therapeutic abortion, or can be procured using a feminine protection pad in the case of a suspected spontaneous abortion. It is important that the test sample be dispersed in a liquid which preserves the sensitive protein analytes as described hereinbefore.

Detection of fetal restricted antigen can be achieved by the methods described hereinbefore. It may be desirable to additionally determine pregnancy using the presence of pregnancy-indicating hormones in serum or urine. Any reliable method can be used, such as those described above with reference to the Ectopic Pregnancy Test.

A test sample obtained during a D&C, therapeutic abortion, or suspected spontaneous abortion (miscarriage) can be tested for the presence of fetal restricted antigen. Concurrent determinations of the presence of pregnancy, and negative determination of fetal restricted antigen in a test sample suspected of representing a therapeutic or spontaneous abortion, is an indication that pregnancy has occurred, and is continuing. Determination of the presence of pregnancy, and positive determination of fetal restricted antigen in a test sample suspected of representing a therapeutic or spontaneous abortion is an indication that pregnancy has occurred, but has been terminated. Determination of the absence of both of pregnancy indicators, and negative determination of fetal restricted antigen in a test sample derived from a D&C is an indication that pregnancy has not occurred, and that no pregnancy has been terminated.

RISK OF PRETERM LABOR/RUPTURED MEMBRANE TEST

An embodiment of this invention for indicating increased risk of preterm birth involves the detection of a fetal restricted antigen in a test sample after week 20 of pregnancy. We have discovered that detectable amounts of these materials are generally absent from vaginal samples such as those obtained from the vicinity of the posterior fornix, cervical canal or cervical os after week 20 of pregnancy. Detectable amounts of these materials present in such samples taken after week 20 pregnancy indicate an increased risk of impending preterm birth and/or indicate the rupture of the amniotic membrane. Since the fetal restricted antigens are not present in significant quantities in the maternal blood, the presence of maternal blood in the sample does not interfere with the test.

A test sample which is to be assayed is removed from the vicinity of the posterior fornix, cervical canal or cervical os, and the sample is assayed to determine the presence or quantity of fetal restricted antigen in the sample as described hereinbefore. A determination of the presence of fetal restricted antigen in a test sample after 20 weeks of pregnancy indicates that fetal membranes may have ruptured, and/or is an indication of increased risk of preterm labor.

INSOLUBLE SUPPORTS

Antigen and antibody reagents of this invention can be bonded to insoluble supports by conventional processes. Antigen binding methods suitable for binding antigens to insoluble supports such as those described in U.S. Pat. Nos. 3,234,096, 3,236,732, 3,309,275, 3,873,683, 3,991,175, 4,003,988, 4,016,250, 4,033,723, 4,071,314, 4,348,207, and 4,419,453, for binding antigens to latex particles and erythrocytes, for example, can be used. Procedures for binding of antibodies to insoluble supports are described in U.S. Pat. Nos. 3,551,555, 3,553,310, 4,048,298 and Re. 29,474, and by Tijsson, PRACTICE AND THEORY OF ENZYME IMMUNOASSAYS. Elsevier Science Publishers, (1985) pp 297-328, for example. Procedures for binding of antibodies to polystyrene by adsorption are described in U.S. Pat. Nos. 3,646,346 and 4,092,408, for example. For purposes of clarity and not by way of limitation, the binding procedures are described herein with respect to the binding of antibodies to insoluble supports. These procedures are suitable for binding of reagent antibodies, such as anti-(fetal restricted antigen) antibodies and anti-(fetal restricted antigen class) antibodies, and for binding of reagent antigens such as reagent fetal restricted antigen to insoluble supports.

A variety of materials can be used as the insoluble support, the primary consideration being the binding of the antibody to the surface, and the absence of interference with the antigen binding reaction or with other reactions which can be employed to determine the presence and extent of the binding reaction. Organic and inorganic polymers, both natural and synthetic, can be used as the insoluble support. Examples of suitable polymers include polyethylene, polypropylene, polybutylene, poly(4-methylbutylene), butyl rubber, silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be used as the insoluble support can the latexes of the above polymers, silica gel, silicon wafers, glass, paper, insoluble protein, metals, metalloids, metal oxides, magnetic materials, semi-conductive materials, cermets and the like. In addition are included substances which form gels, such as proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as phospholipids, long chain (12-24 carbon atoms) alkyl ammonium salts and the like.

A preferred insoluble support of this invention comprises a nylon or nitrocellulose membrane. Alternate insoluble supports are made from a polystyrene, styrene copolymers such as styrene-acrylonitrile copolymers, or polyolefins such as polyethylene or polypropylene, and acrylate and methacrylate polymers and copolymers. The most preferred insoluble supports of this invention are nylon membranes or polystyrene microtiter plates. The reagent antibody or antigen reagents can be bound to the insoluble support by adsorption, ionic bonding, van der Waals adsorption, electrostatic bonding, or other non-covalent bonding, or it can be bound to the insoluble support by covalent bonding.

A particularly advantageous support for this procedure comprises a microtiter plate having a plurality of wells. The well surface or plastic cup inserts therein can constitute the antigen or antibody support. If the determination will require the use of fluorometric measurements, the microtiter plate or the well inserts are advantageously opaque to light so that excitation light applied to a well does not reach or influence contents of the surrounding wells.

Procedures for non-covalent bonding are described in U.S. Pat. No. 4,528,267. Procedures for covalently bonding antibodies and antigens to insoluble supports are described by I. Chibata in IMMOBILIZED ENZYMES. Halsted Press: New York (1978) and A. Cuatrecasas, J. Bio. Chem. 245:3059 (1970). The surface can be coated with a protein and coupled with the antibody or antigen using procedures described in U.S. Pat. No. 4,210,418 using glutaraldehyde as a coupling agent, for example. In an alternate procedure, the well can be coated with a layer having free isocyanate groups such as a polyether isocyanate, and application of the antibody or antigen in aqueous solution thereto effects the requisite bonding. In yet another procedure, the antibody or antigen can be coupled to a hydroxylated material by means of cyanogen bromide as described in U.S. Pat. No. 3,720,760.

The insoluble supports are preferably "blocked" to reduce nonspecific binding. The choice of suitable blocking agents is determined by the type of insoluble support. For example, for polystyrene supports, suitable blocking agents include water-soluble non-immune animal proteins. Suitable water-soluble non-immune animal proteins include bovine serum albumin (BSA); human, rabbit, goat, sheep, and horse serum albumins; casein and non-fat milk; ovalbumin; glycoproteins; and the like. A most preferred blocking/stabilizing solution is 4% sucrose, 1% mannitol, 0.5% casein, 0.01M PBS.

The same blocking agents can also be used for nylon and nitrocellulose supports. However, a preferred blocking agent for nitrocellulose or nylon membrane supports is non-fat milk or casein. An optimum blocking agent for these membrane supports is an aqueous solution containing from 1 to 5 wt. % non-fat dried milk or casein, and nonionic surfactants such as polyoxyethylene sorbitan derivatives and polyoxyethylene ethers.

LABELED REAGENTS

The labeled reagent fetal restricted antigen, anti-(fetal restricted antigen) antibody, anti-(fetal restricted antigen class) antibody and anti-(sandwiching antibody) reagent antibodies of this invention can be prepared by conventional procedures for attaching labels to proteins, preferably with suitable protection of antibody binding sites.

The labels can be bonded or coupled to the protein reagents by chemical or physical bonding. Ligands and groups which can be conjugated to the reagent antigen or antibodies of this invention include elements, compounds or biological materials which have physical or chemical characteristics which can be used to distinguish the reagents to which they are bonded from compounds and materials in the sample being tested.

Labeling procedures are described herein with respect to labeling antibodies for purposes of clarity and not by way of limitation, and the procedures described are generally suitable for labeling any proteinaceous compound or substance, such as the reagent pregnancy antigens or fetal restricted antigens herein.

Radiolabeled antibodies of this invention can be used for in vitro diagnostic tests. The specific activity of a tagged antibody depends upon the half-life, isotopic purity of the radioactive label and how the label is incorporated into the antigen or antibody. Table A lists several commonly used isotopes, their specific activities and half-lives. In immunoassay tests, the higher the specific activity, in general, the better the sensitivity.

TABLE A

| Isotope | Specific Activity of Pure Isotope (Curies/mole) | Half-Life |
|---|---|---|
| $^{14}C$ | $6.25 \times 10^1$ | 5720 years |
| $^3H$ | $2.91 \times 10^4$ | 12.5 years |
| $^{35}S$ | $1.50 \times 10^6$ | 87 days |
| $^{125}I$ | $2.18 \times 10^6$ | 60 days |
| $^{32}P$ | $3.16 \times 10^6$ | 14.3 days |
| $^{131}I$ | $1.62 \times 10^7$ | 8.1 days |

Procedures for labeling antibodies with radioactive isotopes listed in Table A are generally known in the art. Tritium labeling procedures are described in U.S. Pat. No. 4,302,438, for example. Iodinating, tritium labeling and $^{35}S$ labeling procedures especially adapted for antibodies are described by Goding, J., MONOCLONAL ANTIBODIES: PRINCIPLES AND PRACTICE New York: Academic Press (1983) pp 124-126, and the references cited therein. Other procedures for iodinating antibodies are described by Hunter and Greenwood, *Nature* 144:945 (1962) and David et al, *Biochem.* 13:1014-1021 (1974) and in U.S. Pat. Nos. 3,867,517 and 4,376,110. Examples of suitable systems, coupling procedures and substrate reactions therewith are disclosed in U.S. Pat. Nos. Re. 31,006, 3,654,090, 4,214,048, 4,289,747, 4,302,438, 4,312,943, 4,376,110 and the references cited therein, for example. Examples of other suitable systems are described by Pesce et al, *Clin. Chem.* 20:353-359 (1974) and Wisdom, G., *Clin. Chem.* 22:1243 (1976).

A list of suitable enzyme classes which can be used for labeling, and specific examples for each class, follow:

TABLE B

| Class | Enzyme Example |
|---|---|
| Hydrolases | Amylases |
| Nucleases | Polynucleotidase |
| Amidases | Arginase |
| Purine deaminases | Adenase |
| Peptidases | Aminopolypeptidase |
| Proteinases | Pepsin |
| Esterases | Lipases |
| Iron Enzymes | Catalase |
| Copper Enzymes | Tyrosinases |
| Enzymes containing Coenzymes | Alcohol dehydrogenase |
| Enzymes reducing cytochrome | Succinic dehydrogenase |
| Yellow enzymes | Diaphorase |
| Mutases | Glyoxalase |
| Desmolases | Aldolase |
| Oxidases | Glucose oxidase |
|  | Horseradish peroxidase |
| Phosphatases | Alkaline Phosphatases |
|  | Acid Phosphatases |
| Dehydrogenases | G6PDH (Glucose 6 phosphodehydrogenase) |
|  | β-galactosidase |
| Phosphorylases |  |
| Hexokinases |  |

Suitable enzymes are described in Hawk et al, PRACTICAL PHYSIOLOGICAL CHEMISTRY, New York: McGraw-Hill pp. 306-397 (1954).

Fluorogenic and chromogenic enzymes (enzymes in the presence of which a selected substrate will produce a fluorescent or chromogenic product) are useful labeling moieties. Methods for selectively conjugating enzymes to antibodies without impairing the ability of the antibody to bind with antigen and for conjugating enzymes to proteinaceous reagents are well known in the art.

Suitable enzymes and procedures for coupling them to antibodies are described by I. Chibata in IMMOBILIZED ENZYMES. Halsted Press: New York (1978); A. Cuatrecasas, *J. Bio. Chem.* 245:3059 (1970); Wilson, M. et al, INTERNATIONAL CONFERENCE IN IMMUNOFLUORESCENCE AND RELATED STAINING TECHNIQUES. W. Knapp et al, editors. Amsterdam: Elsevier pp. 215-244 (1978); Sullivan, M. et al, *Ann. Clin. Biochem.* 16:221-240 (1979); Nygren, H. et al, *Med. Biol.* 57:187-191 (1979); Gadkari, D. et al, *J. Virol. Meth.* 10:215-224 (1985); Tijssen, P. et al, *Anal. Biochem.* 136:451-457 (1984); Tsuruta, J. et al, *J. Histochem. Cytochem.* 33:767-777 (1985); Ishikawa, E., *J. Immunoassay* 4:209-327 (1983); and in U.S. Pat. No. 4,190,496, for example.

The preferred enzymes and suitable substrates corresponding thereto include horseradish peroxidase for which suitable substrates are o-phenylenediamine, m-phenylenediamine, o-dianisidine, and 4-chloro-α-napthol. They also include β-galactosidase for which suitable substrates are 4-methylumbelliferyl-β-D-galactoside, p-nitrophenyl-β-D-galactose, p-nitrophenol, o-nitrophenyl-β-D-galactose, and o-nitrophenol, for example. They include alkaline phosphatase for which suitable substrates are p-nitrophenylphosphate, indoxyl phosphate, and 5-bromo-3-chloroindoxyl phosphate, for example. A most preferred enzyme substrate combination is alkaline phosphatase and phenolphthalein monophosphate.

Examples of suitable procedures for enzyme labeling the antibody include the use of carbodiimides, daldehydes, and bifunctional coupling reagents. Linkage of enzymes through amide groups can be achieved by treating the proteins with thionyl chloride, N-hydroxysuccinimide or similar reagents in an anhydrous solvent such as dimethylformamide, dioxane, dimethylsulfoxide, tetrahydrofuran, or the like. Alternative coupling agents include carbodiimides such as 1-ethyl-3-(3-(N,N'-dimethylamino)propyl)carbodiimide, 1-cyclohexyl-3-(2-morpholinoethyl)carbodiimide methyl-p-toluenesulfonate, succinimidyl 4-(N-maleimidoethyl)-cyclohexane-1-carboxylate, and succinimidyl 3-(2-pyridyldithio)-propionate, for example.

The carbohydrate moiety of an enzyme can also be oxidized to an aldehyde and reacted with lysyl amino groups of immunoglobulins to form a Schiffs base. Reduction with sodium borohydride effects a stable linkage of enzyme and antibody. Horseradish peroxidase with antibody can be efficiently linked to immunoglobulins by the method of Wilson, M. et al, INTERNATIONAL CONFERENCE IN IMMUNOFLUORESCENCE AND RELATED STAINING TECHNIQUES. W. Knapp et al, editors. Amsterdam: Elsevier pp 215-244 (1978).

Fluorophore and chromophore labeled antibodies can be prepared from standard fluorescent moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, *Science* 162:526 (1968) and Brand, L. et al, *Ann. Rev. Biochem.* 41:843-868 (1972). The antibodies can be labeled with fluorescent chromophore groups by conventional procedures such as those disclosed in U.S. Pat. Nos. 3,940,475, 4,289,747 and 4,376,110, for example.

One group of fluorescers having a number of the desirable properties described above are the xanthene dyes, which include the fluoresceins derived from 3,6-dihydroxy-9-phenylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available.

Another group of fluorescent compounds are the naphthylamines, having an amino group in the alpha or beta position. Included among the naphthylamino compounds are 1-dimethylaminonaphthyl-5-sulfonate, 1-anilino-8-naphthalene sulfonate and 2-p-toluidinyl-6-naphthalene sulfonate. Other dyes include 3-phenyl-7- isocyanatocoumarin; acridines such as 9-isothiocyanatoacridine and acridine orange; N-[p-(2-benzoxazolyl)phenyl]maleimide; benzoxadiozoles such as 4-chloro-7-nitrobenzo-2-oxa-1,3-diazole and 7-(p-methoxybenzylamino)-4-nitrobenzo-2-oxa-1,3-diazole; stilbenes such as 4-dimethylamino-4'-isothiocyanatostilbene and 4-dimethylamino-4'-maleimidostilbene; N,N'-dioctadecycloxacarboxyamine-p-toluenesulfonate; pyrenes such as 8-hydroxy-1,3,6-pyrenetrisulfonic acid, 1-pyrenebutyric acid, merocyanine 540, rose bengal, 2,4-diphenyl-3(2H)-furanone, o-phthaldehyde, as well as other readily available fluorescing molecules. These dyes either have active functionalities or such functionalities can be readily introduced.

Antibodies can be labeled with fluorochromes or chromophores by the procedures described by Goding, J., MONOCLONAL ANTIBODIES: PRINCIPLES AND PRACTICE. New York: Academic Press (1983) pp 208-249. The concentration of fluorochrome is selected according to the table of Goding, supra, p 229. For example, fluorescein isocyanate (1.0 mg/mL) or rhodamine isocyanate (10.0 mg/mL) in DMSO is prepared, and the desired volume (1-10% of total protein solution volume) is added to the protein solution dropwise, with stirring. The reaction proceeds for two hours, shielded from light. The product is purified by gel filtration on SEPHADEX G-25 gel in PBS containing 0.1% $NaNO_3$ to separate the unreacted or hydrolyzed fluorochrome. The absorbance of the conjugate is measured at 280 nm and at its peak in the visible region (495 nm for fluoresceinated antibody and 550 nm for rhodaminated antibody). The fluorochrome to protein ratio is calculated according to the procedure of Goding, MONOCLONAL ANTIBODIES: PRINCIPLES AND PRACTICE. New York Academic Press (1983) pp 224-225. Conjugates are stored at 4° C. protected from light until use. If the antibody solution concentration is less than 1 mg/mL, BSA is added to the solution to a final concentration of 1 mg/mL.

The antibodies and reagent antigens used in the assays of this invention can be covalently bonded to avidin or biotin. Suitable binding procedures involve cross-linking through a bifunctional cross-linking agent. Suitable bifunctional compounds are described by Peters, K. et al, Ann. Rev. Biochem. 46:523 (1977). Alkyl imidates show a high degree of specificity among the functional groups presented to them by a protein. The reaction is specific for primary amino groups. Examples of suitable coupling reagents include amidoesters such as dimethylmalonimidate, azides such as the acyl azide of tartryl diazide which reacts readily with immuno groups to produce amide linkages. Aryl dihalides (e.g., 1,5-difluoro-2,4-dinitrobenzene, or 4,4'-difluoro- 3,3'-dinitrophenyl sulfone, glutaraldehyde, 1-ethyl-3-(3-dimethylaminopropyl)carbodiimide hydrochloride, dimaleimide, mixed anhydride, m-maleamidobenzoyl N-hydroxysucciinimide ester, and other known cross-linking agents can be used.

The foregoing reagents provide essentially irreversible bonds. Bifunctional agents with functional groups such as disulfide or glycol may be used. These provide bonds which can be broken after the cross-linking reaction, if desired. Such reagents include dimethyl 3,3'-dithiobispropionimidate, succinimidylpropionimidate, N-(3-fluoro-4,6-dinitrophenyl)cystamine, tartryl diazide, tartryl di(glycylazide) and tartryl di(epsilon-amino caproylazide).

In other instances, the bonds can be formed directly between the reagents themselves. For example, antibody can be bound to biotin through functional groups on the respective materials. As a specific example, biotin can be treated with periodate and reacted with antibody to give a Schiff base formation without inhibiting the biotin to avidin binding or blocking immunological activity of the antibody. Avidin-conjugated and biotinylated reagents are available from Vector Laboratories, Burlingame, Calif.

Known techniques using bifunctional cross-linking agents include the following: (a) a one-step glutaraldehyde linkage, Avrameas, S., Immunochem. 6:43 (1969); (b) two-step glutaraldehyde linkage, Avrameas, S., Immunochem. 8:1175 (1971); and (c) dimaleimide linkage, Kato, K. et al, Euro. J. Biochem. 62:285 (1966).

Antibodies can be labeled with metallic radionuclides according the procedure of Hnatowich, D. et al. J. Appl. Rad. 35:554-557 (1984) and Buckley, R et al. Fed. Eur. Biochem. Soc. 166:202-204 (Jan. 1984). In this procedure the antibodies are conjugated with a chelating agent, such as diethylenetriaminepentaacetic acid (DTPA), which is capable of forming a chelate with the metallic radionuclide. A suspension of 0.1 mg/mL of the bicyclic anhydride of DTPA is prepared in a dry solvent such as chloroform, ether or dry DMSO. An aliquot is removed to a clean, dry tube sufficient to provide a DTPA to immunoglobulin molar ratio of 1:1 and evaporated under nitrogen. A 10-20 microliter portion of the antibody solution used (10-20 mg/mL) in 0.05M bicarbonate buffer in saline, pH 7.0-7.5, is added to the dry DTPA, and the contents are agitated for 0.5-1.0 minute. The coupled protein preparation is diluted to 0.2 mL with the same buffer solution and purified on a 5 cm gel filtration column with SEPHADEX G-50 gel, using a saline eluant. The coupling efficiency is determined before purification by the addition of "chelation-grade" $^{111}In$ in 0.5M acetate buffer solution, pH 6.0. Thin layer chromatography is used to separate the DTPA coupled antibody for calculation of the coupling efficiency. The DTPA-coupled antibodies can be stored at 4° C. until needed for binding with metallic radionuclides such as $^{111}IN+3$, $^{212}Bi+3$ and $^{68}Ga+3$, for example.

This invention is further illustrated by the following specific, but non-limiting examples. Temperatures are given in degrees Centigrade and percents as weight percents unless otherwise specified.

EXAMPLE 1

Polyclonal Anti-(fetal fibronectin) Antibody

Fetal fibronectin is purified from amniotic fluid as described by Engall and Ruoslahti, Int. J. Cancer 20:1-5 (1977).

The anti-(fetal fibronectin) antibodies are elicited in rabbits using the immunization techniques and schedules described in the literature, e.g., Stollar, Meth. Enzym. 70:70 (1980), immunizing the rabbits with the fetal fibronectin antigen. The antiserum is screened in a solid phase assay similar to that used for monoclonal antibodies, e.g., as described by Lange et al, Clin. Exp. Immunol. 25:191 (1976) and Pisetsky et al, J. Immun. Meth. 41:187 (1981).

The IgG fraction of the antisera is purified further by affinity chromatography using CNBr-Sepharose 4B (Pharmacia Fine Chemicals) to which has been coupled fetal fibronectin. The method used for coupling is that recommended by the gel manufacturer, AFFINITY CHROMATOGRAPHY. Pharmacia Fine Chemicals, pp 15–18.

The column is equilibrated with from 2 to 3 volumes of buffer (0.01M PBS, pH 7.2), and the anti-(fetal fibronectin) antibody containing solution is then applied to the column. The absorbency of the eluate is monitored at 280 nm until protein no longer passes from the column. The column is then washed with 0.1M glycine buffer, pH 2.5, to desorb the immunoaffinity bound anti-(fetal fibronectin) antibody. Peak protein fractions are collected, pooled and dialyzed against 0.01M PBS, pH 7.2, for 24–36 hr at 4° C. with multiple buffer changes.

If a higher purity is desired, the affinity purified IgG can be passed through an adult plasma fibronectin bound affinity column by the procedure described above to remove any antibodies which would cross-react with adult plasma fibronectins.

EXAMPLE 2

Monoclonal Anti-(fetal fibronectin) Antibody

Using the purified fetal fibronectin obtained by the procedure of Example 1, mouse monoclonal antibodies to the fetal fibronectin are obtained using standard procedures of Galfre and Milstein, Meth. Enzym. 73:1 (1981) and Matsuura, H. and Hakomori, S. et al, Proc. Natl. Acad. Sci. USA 82:6517–6521 (1985), using fetal fibronectin as the antigen for immunizing the mice. The monoclonal antibodies are screened using a modification of the techniques described in the literature, e.g., Lange et al, Clin.Exp.Immunol. 25:191(1976) and Pisetsky et al, J. Immun. Meth. 41:187 (1981).

Mouse monoclonal antibody is purified from ascites fluid or from hybridoma culture supernatants using Protein-A coupled Sepharose-4B (Pharmacia Fine Chemicals) according to the procedure of Tijsson, PRACTICE AND THEORY OF ENZYME IMMUNOASSAYS. Elsevier Science Publishers, pp 105–107 (1985).

EXAMPLE 3

Polyclonal Anti-(fetal fibronectin) Antibody-Coated Microtiter Plate

Rabbit anti-(fetal fibronectin) prepared and further purified to remove adult fibronectin cross-reactivity as described in Example 1 is diluted to 10 μg/mL in 0.05M carbonate buffer, pH 9.6. 100 μL is dispersed into each well of an IMMULON II microtiter plate (Dynatech). The plate is covered and incubated 4 hr at room temperature or 4° C. overnight. The plate is washed 4 times with Wash Buffer (0.02M Tris HCl, 0.015M NaCl, 0.05% TWEEN-20), filling and emptying the wells completely with each use. The plate is then blocked by dispersing into each well 200 μL of a blocking solution (0.01M PBS, 1% BSA, 0.02% NaN$_3$, pH 7.4) and incubating for 1 hr at room temperature. The wells are then washed 4 times with Wash Buffer, as described above. The plate is now ready for immunoassay of samples.

EXAMPLE 4

Polyclonal Anti-Human Fibronectin Antibody

Human plasma fibronectin was purified from human plasma as described by Engvall and Ruoslahti, Int. J. Cancer 20:1–5 (1977).

The anti-human plasma fibronectin antibodies were elicited in goats using the immunization techniques and schedules described in the literature, e.g., Stollar, Meth. Enzym. 70:70 (1980), immunizing the goats with the human plasma fibronectin antigen. The antiserum was screened in a solid phase assay similar to that used for monoclonal antibodies, e.g., as described by Lange et al, Clin. Exp. Immunol. 25:191 (1976) and Pisetsky et al, J. Immun. Meth. 41:187 (1981).

The IgG fraction of the antiserum was purified further by affinity chromatography using CNBr-Sepharose 4B (Pharmacia Fine Chemicals) to which has been coupled human plasma fibronectin according to the method recommended by the manufacturer (AFFINITY CHROMATOGRAPHY, Pharmacia Fine Chemicals Catalogue 1990), pp 15–18.

Briefly, the column was equilibrated with from 2 to 3 volumes of buffer (0.01M PBS, pH 7.2), and the anti-human fibronectin antibody-containing solution was then applied to the column. The absorbency of the effluent was monitored at 280 nm until protein no longer passed from the column. The column was then washed with equilibration buffer until a baseline absorbance at 280 nm was obtained.

The immunoaffinity bound anti-human plasma fibronectin antibody was eluted with 0.1M glycine buffer, pH 2.5. Peak protein fractions were collected, pooled and dialyzed against 0.01M PBS, pH 7.2, for 24–36 hr at 4° C. with multiple buffer changes.

The above procedure was repeated to immunize rabbits with human plasma fibronectin and to purify the resultant polyclonal anti-human fibronectin antibodies.

EXAMPLE 5

Polyclonal Anti-Fibronectin

Antibody-Coated Microtiter Plate

Goat anti-human plasma fibronectin prepared as described in Example 4 is diluted to 10 μg/mL in 0.05M carbonate buffer, pH 9.6. 100 μL is dispersed into each well of a polystyrene microtiter plate such as supplied by Costar, Nunc, or Dynatech. The plate is covered and incubated 2 to 4 hr at room temperature or 4° C. overnight. The plate is washed 3 to 4 times with Wash Buffer (0.02M Tris HCl, 0.015M NaCl, 0.05% TWEEN-20), filling and emptying the wells completely with each use. The plate is then blocked by dispersing into each well 200 μL of a blocking/stabilizing solution (4% sucrose, 1% mannitol, 0.01M PBS, 1% BSA, 0.02% NaN$_3$, pH 7.4) and incubated for 30 minutes to 2 hrs at room temperature. The wells are then aspirated to dryness, the plate is packaged in an air-tight container with a desiccant pouch, and stored at 4° C. until needed.

EXAMPLE 6

Monoclonal Antibodies from Hybridoma HB 9018

Preparation of the Hybridoma deposited at the American Type Culture Collection and given the accession number ATCC HB 9018 is described in detail in U.S. Pat. No. 4,894,326 issued Jan. 16, 1990 to Matsuura et al, which patent is incorporated herein by reference in its entirety.

The hybridoma was cultured by growth in RPMI 1640 tissue culture medium supplemented with 10% fetal bovine serum. Additionally, the hybridoma was cultured in mice by the injection of the hybrid cells according to the procedure of Mishell and Shiigi (Selected Methods in Cellular Immunology, W.H. Freeman & Co, San Francisco p 368, 1980).

The monoclonal antibody designated FDC-6 and produced by the hybridoma was prepared for use in an immunoassay by the following procedure. The IgG fraction of the culture supernatant or the ascites was precipitated by ammonium sulfate fractionation. The antibody was redissolved and dialyzed into the appropriate buffer for purification by affinity chromatography on Protein-G Fast Flow (Pharmacia Fine Chemicals) according to the manufacturer's directions.

EXAMPLE 7

Monoclonal Antibody-Coated Microtiter Plate

Microtiter plates were coated with FDC-6 monoclonal antibody by following the procedure described below.

Monoclonal antibody FDC-6 prepared as described in Example 6 was diluted to 10 µg/ml in phosphate buffer, pH 7.2 and 100 µl/well was dispersed into a polystyrene microtiter plate (Costar). The plates were incubated for 2 hours at room temperature or overnight at 4° C. The contents of the wells were aspirated and the wells washed 3 to 4 times with wash buffer (0.02M Tris HCl, 0.015M NaCl, 0.05% TWEEN-20) as described in Example 5.

200 µl/well of blocking/stabilizing solution (4% sucrose, 1% mannitol, 0.5% casein, 0.01M PBS) was then added to the wells and incubated for 30 minutes to 4 hours at room temperature. The wells were then aspirated to dryness, and the plate was packaged in an airtight container with a desiccant pouch, and stored at 4° C. until needed.

The above procedure was repeated using microtiter plates from Nunc and Dynatech and gave equivalent results.

EXAMPLE 8

Enzyme Labeled Anti-(fibronectin) Antibody

Anti-human plasma fibronectin antibody prepared according to Example 4 was conjugated with alkaline phosphatase following the one-step glutaraldehyde procedure of Avrameas, *Immunochem.* 6:43 (1969).

EXAMPLE 9

Fetal Fibronectin Assay Kit and Method

In a preferred embodiment, an assay kit for the fetal restricted antigen, fetal fibronectin included the following reagents:
1. a microtiter plate coated with murine monoclonal anti-fetal fibronectin antibody.
2. alkaline phosphatase-conjugated, affinity purified, polyclonal, goat anti-fibronectin antibodies
3. enzyme substrate
4. a negative control
5. a positive control
6. rinse buffer concentrate (50X)

The microtiter plate coated with murine monoclonal anti-fetal fibronectin antibody and the alkaline phosphatase-conjugated, affinity purified, polyclonal, goat anti-fibronectin antibodies were prepared as described in Examples 7 and 8, respectively. The microtiter plate was packaged as 12 strips of eight wells each in sealed plastic bags containing desiccant.

The stock antibody conjugate was appropriately diluted in conjugate diluent (0.05M Tris Buffer pH 7.2, 2% D-Sorbitol, 2% BSA, 0.1% Sodium Azide, 0.01% Tween-20, 1 mM Magnesium Chloride, and 0.1% Zinc Chloride) and 10 ml placed in a polyethylene dropper bottle container.

The enzyme substrate (10 mL in a polyethylene dropper bottle container) was phenolphthalein monophosphate (1 mg/ml) dissolved in 0.4M aminomethylpropanediol buffer, pH 10 with 0.1 mM magnesium chloride and 0.2% sodium azide.

The positive control (2.5 mL in a polyethylene dropper bottle container) was amniotic fluid containing fetal fibronectin diluted to a concentration of fetal fibronectin of 50 ng/mL in sample diluent solution (0.05M Tris buffer pH 7.4, 1% bovine serum albumin (BSA), 0.15M sodium chloride, 0.02% Sodium Azide, 5 mM ethylenediamine tetraacetic acid (EDTA), 1 mM phenylmethylsulfonyl fluoride (PMSF), and 500 Kallikrein Units/ml of Aprotinin). This sample diluent solution is described in U.S. Pat. No. 4,919,889 to Jones et al, issued Apr. 24, 1990, which patent is incorporated herein by reference in its entirety.

The negative control (2.5 mL in a polyethylene dropper bottle container) was the sample diluent solution used for the positive control without fetal fibronectin.

The rinse buffer (10 mL in a polyethylene dropper bottle container) was a 50X concentrate containing 1.0M Tris buffer pH 7.4, 4.0M sodium chloride, 2.5% Tween-20, and 1% sodium azide. The rinse buffer was diluted with water to a final concentration of 0.02M Tris, 0.08M sodium chloride, 0.05% Tween-20, and 0.02% sodium azide for use in the assay.

The kit additionally contained 24 5µ pore size polyethylene sample filters (Porex Technologies, Fairburn, Ga.), a microtiter strip holder, a microtiter plate cover and an instruction sheet. All of the dropper bottles in the kit were polyethylene bottles designed to dispense approximately 50 µL drops of the reagent. All of the assay steps performed following sample collection utilized the reagents and materials in the kit.

The assay was performed as follows. All samples were collected in the vicinity of the posterior fornix or cervical os using dacron swabs. Swab samples were immersed in 1.0 mL of sample diluent in a collection vial. The sample diluent solution is described above. The swabs were removed from the solution leaving as such liquid as possible in the collection tube. The samples were incubated at 37° C. along with the controls from the assay kit for 15 minutes prior to the assay, either before or after filtration. A sample filter was snapped in place on each sample tube. The 8-well strips were snapped into place in a strip holder. The holder had the alphanumeric indications of the 12 columns and eight rows of standard microtiter plates. Duplicate 100 µL aliquots of each sample and the positive and negative controls were placed in separate wells of the microtiter strip and incubated for 1 hour at room temperature.

Following incubation, samples and controls were aspirated from the wells. Wells were washed three times with diluted wash buffer (1X). Following washing, 100 µL of enzyme-antibody conjugate was added to each well and incubated for 30 minutes at room temperature. The wells were aspirated and washed as described above. Following washing, 100 µL of enzyme substrate was added to each well and incubated for 30 minutes at room temperature.

Following the incubation, the plates were gently agitated by hand or with an orbital shaker to mix the well contents. The frame of strips was placed in an ELISA plate reader. The absorbance of each well at 550 nm was determined. The average absorbance of the duplicate wells for each sample and control was calculated. If the absorbance of the patient sample was less than the absorbance of the positive control, the sample was negative, indicating an undetectable level of fetal fibronectin in the sample. If the sample absorbance is greater than or equal to the absorbance of the positive control, the sample was positive, indicating that fetal fibronectin was present in the sample. In any assay if the absorbance of the positive control was not greater than 1.5 times the absorbance of the negative control the results were discarded and the assay procedure was repeated.

EXAMPLE 10

Pregnancy Test

To perform the pregnancy test, a sample is removed from the vaginal cavity in the vicinity of the cervical canal or cervical os, and assayed to determine the presence of the fetal restricted antigen, fetal fibronectin from a woman who is suspected of being pregnant. Samples obtained before week 20 of pregnancy which demonstrate significant fetal fibronectin in the test sample indicate normal uterine pregnancy.

Swab samples were obtained from 393 women as described in Example 9. Of the women tested 50 were confirmed as non-pregnant (NP) (by analysis of serum or urine human chorionic gonadoropin [hCG]); 333 were confirmed to have intra-uterine pregnancies (IUP) (by analysis of serum or urine hCG); and 10 were confirmed to have ectopic pregnancies (ECT) (by medical history, serum hCG, clinical examination and surgical confirmation).

The assay was performed as described in Example 9 with the following exceptions. The antibody conjugate was goat anti-human fibronectin (Jackson ImmunoResearch Labs catalogue no. 109-056-059) diluted 1:1,000 in 0.02M Tris, 0.3 m NaCl, 0.05% Tween 20, 5.0% BSA, 0.02% NaN. The enzyme substrate was para-nitrophenyl phosphate (Sigma Chemical Co. catalogue no. 104-40T) diluted in AMP buffer (Sigma Chemical Co. catalogue no. 221). In addition, the samples were centrifuged rather than filtered to remove particulates. For this test, an assay which detected any fetal fibronectin in the sample was scored as a positive test. The results of the tests are illustrated below.

| Population | fFn − | fFn + |
|---|---|---|
| NP = 50 | 42 | 8 |
| IUP = 333 | 72 | 261 |
| ECT = 10 | 3 | 7 |
| Preg = 343 | 75 | 268 |

Analyses of the test results are illustrated below. The first analysis does not include the results from women with ectopic pregnancies. The second analysis includes results from women with ectopic pregnancies. In the analyses, the following abbreviations were used. "Se" means sensitivity (the number of true positive test results divided by the total number of women with the condition; i.e., the number of true positive test results divided by the the sum of the number of true positive and false negative test results). "Sp" means specificity (the number of true negative test results divided by the total number of women without the condition; i.e., the number of true negative test results divided by the sum of the number of true negative and false positive test results). "PPV" means positive predictive value (the number of true positive test results divided by the total number of samples which tested positive). "NPV" means negative predictive value (the number of true negative test results divided by the total number of samples which tested negative).

|  | fFn − | fFn + |  |
|---|---|---|---|
| NP | 42 | 8 | 50 |
| IUP | 72 | 261 | 333 |
|  | 114 | 269 | 383 |

Se = 261/333 = 78%
Sp = 42/50 = 84%
PPV = 261/269 = 97%
NPV = 42/114 = 37%

|  | fFn − | fFn + |  |
|---|---|---|---|
| NP | 42 | 8 | 50 |
| PREG | 75 | 268 | 343 |
|  | 117 | 276 | 393 |

Se = 268/343 = 78%
Sp = 42/50 = 84%
PPV = 268/276 = 97%
NPV = 42/117 = 36%

The results of the studies demonstrate that a positive assay result indicates that a woman is pregnant.

EXAMPLE 11

Ectopic Pregnancy Test

The procedure of Example 10 was repeated using the same samples. However, in this case, a cutoff of 0.5 µg/ml of fetal fibronectin (the value of a negative control plus two standard deviations) was used for a positive test result for the presence of fetal fibronectin. The data was analyzed as described in Example 10. Sensitivity, specificity, positive predictive value and negative predictive value are based on detection of ectopic pregnancy in this analysis.

Preg:

|  | fFn − >.5 | fFn + ≤.5 |  |
|---|---|---|---|
| NOT ECT | 135 | 198 | 333 |
| ECT | 0 | 10 | 10 |
|  | 135 | 208 | 343 |

↑
TOTAL PREG

Se = 10/10 = 100%
Sp = 135/333 = 41%
PPV = 10/208 = 5%
NPV = 135/135 = 100%

The results demonstrate that a positive test result provides a high degree of confidence that a woman does not have an ectopic pregnancy. This is, for these samples 100% of the test results indicating that a woman had an intra-uterine pregnancy were correct. The test can therefore be characterized as a "Rule in IUP" test; Specifically, a fetal fibronectin concentration of >0.5 µg/ml indicates an intra-uterine pregnancy.

EXAMPLE 12

Product of Therapeutic Abortion Test

Samples obtained from a therapeutic abortion were tested to verify that fetal materials had been removed from the uterus. The assay was performed as in Example 9 with the following exceptions. The samples were prepared as follows. Samples were collected from products of conception by aqueous filtration through woven cotton into a test tube, centrifuged at 2000 rpm for 10 minutes and the supernatants assayed directly for fetal fibronectin with no further dilution. A calibration curve was included in the test. The calibrators were diluted from amniotic fluid of known fetal fibronectin concentration to an assay range of from 10 ng/mL to 4 mg/mL. Sample diluent solution was used as the negative background control. The samples were assayed as described in Example 9 using the calibration curve to quantify the fetal fibronectin concentration. A fibronectin cutoff of 0.11 µg/ml (negative control value plus 2 standard deviations) was used to determine positivity.

In this study, D&C materials from 291 women with confirmed intra-uterine pregnancies and 8 women without uterine pregnancies (2 ectopically pregnant and 6 nonpregnant women were evaluated). The results are illustrated below.

|  | fFn + ≥.11 | fFn − <.11 |  |
|---|---|---|---|
| POC | 288 | 3 | 291 |
| CONTROL | 0 | 8 | 8 |
|  | 288 | 11 | 299 |

Se = 288/291 = 99%
Sp = 8/8 = 100%
PPV = 288/288 = 100%
NPV = 8/11 = 72.7%

In samples containing products of conception, significant amounts of fetal fibronectin were found, confirming the existence of normal pregnancy and the termination thereof. The data also demonstrate that in a pregnant patient having a negative assay result, the possibility of an ectopic pregnancy is indicated.

EXAMPLE 13

Preterm Labor Sandwich Immunoassay

The procedure of Example 9 was repeated with test samples obtained during weeks 20-36 of pregnancy. Studies were conducted at three perinatal referral clinics in the United States. Women were evaluated for admission to the hospital for either suspected preterm rupture of membranes or suspected preterm labor with intact membranes.

Confirmation of rupture of membranes was made by visual examination of the vagina for gross pooling of amniotic fluid, microscopic examination of dried vaginal secretions for ferning, presence of alkaline vaginal secretions using nitrazine paper and ultrasound diagnosis of oligohydramnios. Rupture of membranes was defined by the presence of any two of these four diagnostic criteria. One hundred-seventeen women with intact amniotic membranes pregnant between 23 weeks and 36 weeks, 6 days of gestation based on last known menstrual period and expected date of confinement confirmed by first trimester pelvic examination and ultrasonography <28 weeks gestation are subsequently described. Women were determined by the attending physician to be at risk for preterm labor and subsequent delivery based on medical history and clinical examination including recording of uterine contractions and examination of the cervix. Since the clinical definition of preterm labor is sometimes difficult to establish, data establishing the clinical utility of fetal fibronectin were analyzed using preterm delivery as the outcome variable.

To assess the potential for cervicovaginal contamination by maternal plasma fibronectin, maternal blood specimens were obtained from 52 women with apparently healthy pregnancies during second or third trimester. Amniotic fluid specimens were obtained from 92 patients undergoing amniocentesis for genetic diagnosis in early second trimester and 8 patients undergoing amniocentesis for evaluation of fetal lung maturity prior to elective repeat, cesarean section in third trimester.

The assay results indicated that the concentration of fetal fibronectin in amniotic fluid in second trimester was 87.1±4.8 µg/ml (n=92) and 27.1±17.3 µg/ml (n=8) in third trimester. The concentration of fetal fibronectin in maternal plasma in the second trimester was 1.48±0.11 µg/ml (n=20) and 3.19±0.30 µg/ml (n=32) in the third trimester.

|  | fFn + | fFn − |  |
|---|---|---|---|
| PTD | 49 | 10 | 59 |
| TD | 11 | 47 | 58 |
|  | 60 | 57 | 117 |

+Sensitivity = 83.1%, Specificity = 81.7%
Relative Risk Ratio = 20.9 (95% CI:8.8, 49.7); $X^2$, p < 0.01

As is shown in the table above for the 117 patients with suspected preterm labor and intact amniotic membrnes, 49 of 59 (sensitivity=83.1%) women delivering prematurely (PTD) had fetal fibronectin in their cervicovaginal secretions compared to 11 of 58 women (specificity=81.0%) delivering at term (TD) (p<0.01). Similarly, those patients with fetal fibronectin in their cervicovaginal secretions were far more likely to deliver prematurely (positive predictive value=81.7%) than those women not expressing cervicovaginal fetal fibronectin (negative predictive value=82.5%).

The presence of cervicovaginal fetal fibronectin was a sensitive and specific predictor of the risk for preterm delivery in these women with suspected preterm labor. The presence of fetal fibronectin in these patients was strongly associated with risk of preterm delivery with a logistic regression odds ratio of 3.79 (95% CI:2.33, 6.15; p<0.01).

To evaluate for potential confounding by fetal fibronectin of maternal origin, the data was analyzed after exclusion of 31 samples contaminated with blood. As shown below, similar proportions of patients had fetal fibronectin in their cervicovaginal secretions and delivered prematurely. Furthermore, inclusion of the presence or absence of vaginal bloody show into the stepwise logistic regression model gave an odds ratio of 1.70 (95%CI: 0.91,3.18; p=0.1) demonstrating that bloody show was not an independent predictor of preterm delivery after fetal fibronectin was introduced into the model. It was clear, however, from univariate analysis that detection of fetal fibronectin in cervicovaginal secretions contaminated with blood is an indicator of imminent delivery.

|     | fFn + | fFn − |    |
|-----|-------|-------|----|
| PTD | 27    | 9     | 36 |
| TD  | 7     | 43    | 50 |
|     | 34    | 52    | 86 |

+Sensitivity = 75.0%, Specificity = 86.0%
Relative Risk Ratio = 18.4 (95% CI:6.7, 50.4); $X^2$, $p < 0.01$ The utility of fetal fibronectin for identifying women at risk for PTD was maintained even when women in preterm contractions with intact membranes with cervical dilation exceeding 2 cm were eliminated from the analysis. The logistic regression odds ratio of 3.18 (95%CI: 1.8,5.6, $p<0.01$) confirmed the predictive value of fetal fibronectin in this clinically discrete population.

|     | fFn + | fFn − |    |
|-----|-------|-------|----|
| PTD | 20    | 8     | 28 |
| TD  | 8     | 41    | 49 |
|     | 28    | 49    | 77 |

+Sensitivity = 71.4%, Specificity = 83.7%
Relative Risk Ratio = 12.8 (95% CI:4.5, 36.3); $X^2$, $p < 0.01$

EXAMPLE 14

Ruptured Membranes Sandwich Immunossay

The procedure of Example 9 was repeated with test samples obtained from week 20 of pregnancy to term. The purpose of this multisite clinical study was to evaluate the efficacy of the immunoassay to detect fetal fibronectin in vaginal secretions of women with term pregnancies and suspected rupture of membranes (TROM), women with preterm pregnancies and suspected rupture of membranes (PROM) and pregnant women in third trimester with intact amniotic membranes (CONTROL). The tenative diagnosis of rupture of amniotic membranes was made according to the clinical criteria outlined in Example 13. The assay results were analyzed for each group by demographic characteristics, obstetrical history and salient features of the current pregnancy including interval between sample collection and delivery. Fetal fibronectin was analyzed in cervicovaginal secretions obtained from 85 women in PROM, 339 women in TROM and 67 women in CONTROL. Only data for women with known gestational ages as confirmed by ultrasonography or last known menstrual period who gave informed consent are subsequently described.

The following table shows the number of observations and means (±SD) for gestational ages (weeks) at sampling (EGAS) and delivery (EGAD) and the interval between sampling and delivery (SAMDEL) for women in PROM, TROM and CONTROL partitioned by fetal fibronectin result. Data is also provided for TROM and CONTROL describing the percentage of deliveries occuring within 48 hours of sampling (%Del<48Hrs) and the percentage of preterm deliveries in PROM (%PTD).

|              | PROM  |       | TROM  |       | CONTROL |       |
|--------------|-------|-------|-------|-------|---------|-------|
|              | fFN + | fFN − | fFN + | fFN − | fFN +   | fFN − |
| n            | 80    | 5     | 319   | 20    | 13      | 54    |
| EGAS         | 32.3  | 30.4  | 39.3  | 38.9  | 38.6    | 38.4  |
| (Weeks)      | (3.8) | (4.5) | (1.8) | (1.3) | (1.4)   | (1.5) |
| EGAD         | 32.7  | 33.5  | 39.4  | 39.9  | 39.6    | 40.3  |
| (Weeks)      | (4.0) | (6.0) | (1.8) | (1.4) | (1.8)   | (1.5) |
| SAMDEL       | 59.0  | 542.0 | 18.1  | 163.4 | 169.3   | 333.4 |
| (Hours)      | (204) | (439) | (48)  | (182) | (165)   | (213) |
| % Del < 48 Hrs | —   | —     | 94.7  | 45.0  | 23.1    | 5.3   |
| % PTD        | 97.5  | 60.0  | —     | —     | —       | —     |

Of the 85 patients in PROM with suspected preterm rupture of membranes, 80 had fetal fibronectin in their cervicovaginal fluid and 97.5% (n=78) delivered prematurely indicating that the amniotic membranes were ruptured. Of the 339 patients in TROM with suspected term rupture of membranes, 319 had fetal fibronectin in their cervicovaginal fluid and 94.7% (n=302) delivered within 48 hours of sampling indicating that the amniotic membranes were ruptured.

Of the 67 patients in CONTROL with apparently intact amniotic membranes, 13 had fetal fibronectin in their cervicovaginal fluid and 23.1% delivered within 48 hours of sampling compared to 5.3% for the women in CONTROL with negative fetal fibronectin results. These results indicate that conventionally used diagnostic tests for detection of rupture of membranes are frequently unreliable. Moreover, all women with positive fetal fibronectin results had significantly ($p<0.05$) shorter sample to delivery intervals than women with negative fetal fibronectin results.

Of the 339 samples collected from women in TROM, information regarding the presence of vaginal bloody show was available for 316. Of these, 90 (28.5%) were collected in the presence of vaginal bloody show. EGAS, EGAD, SAMDEL and %Del<48 hrs are shown for these women in the following table. While EGAS and EGAD are similar for women with and without vaginal bloody show, women with vaginal bloody show deliver more quickly than those without blood in the vagina ($p<0.05$). The proportion of positive results is similar regardless of the presence or absence of blood in the vagina at the time of specimen collection.

|              | TROM    |         |
|--------------|---------|---------|
|              | Blood + | Blood − |
| n            | 90      | 226     |
| EGAS         | 39.3    | 39.3    |
| (Weeks)      | (1.0)   | (1.1)   |
| EGAD         | 39.4    | 39.4    |
| (Weeks)      | (1.1)   | (1.2)   |
| SAMDEL       | 12.8    | 28.1    |
| (Hours)      | (23.7)  | (111)   |
| % Del < 48 Hrs | 91.2  | 95.6    |

This analysis demonstrates that the presence of blood in vaginal secretions has no apparent effect on test outcome for this population of women. Only one woman in CONTROL was identified as having vaginal bloody show. She had a negative assay result and delivered approximately 135 hours following specimen collection.

Fetal fibronectin is an optimal marker for detection of amniotic fluid indicating rupture of amniotic membranes. Fetal fibronectin is present in amniotic fluid in high concentration and in the maternal blood in low concentration. Immunologic detection of fetal fibronectin in cervicovaginal fluid is a safe and effective method for identifying the presence or absence of amniotic fluid in the vagina to determine if the amniotic membranes have been compromised.

EXAMPLE 15

Fetal Fibronectin Assay Kit and Method

In another preferred embodiment, an assay kit for the fetal restricted antigen, fetal fibronectin included the following components. This kit was designed to be used to perform a rapid, bedside assay.

1. an assay device comprising a plastic housing and containing: (a) a porous nylon membrane to which is bound a monoclonal anti-fetal fibronectin antibody; (b) a flow control membrane system; and (c) an absorbent layer
2. a colloidal gold-labeled goat anti-fibronectin antibody conjugate in a protein matrix
3. conjugate reconstitution buffer
4. a wash solution
5. a sterile, dacron sample collection swab The membrane device was prepared by the following procedure. Approximately 2 μL of the murine monoclonal antibody FDC-6 prepared as described in Example 6 is applied to a membrane surface (1.2μ nylon, Biodyne-A, Pall) in a pH 6, 0.01M phosphate buffered saline (PBS), 0.1M citrate buffer containing 0.5 mg/ml BSA. A procedural control consisting of human plasma fibronectin purified as described in Example 4 in the same buffer is also applied to a discrete region of the membrane. After the membrane has air dried, a blocking reagent of PBS-buffered, 0.5% nonfat dry milk is added to the membrane. The excess blocking reagent is removed after at least about 20 minutes.

The membrane-holding device (Target Device, V-Tech, Pomona, Calif.) is assembled with a second porous layer (0.45μ low protein-binding nylon, Lo-Prodyne, Pall) beneath the antibody-bearing membrane (in the direction of sample application) for controlling the flow of sample solution from the assay membrane to the absorbent layer. The two porous membranes are then placed over an absorbent porous polyethylene layer having a capacity of greater than 1.5 ml (Chromex, Brooklyn, N.Y.) and enclosed in the device. The device is packaged individually in a sealed plastic bag containing desiccant.

The colloidal gold is prepared by the reduction of 0.01% tetrachloroauric acid with 0.16% sodium citrate in a manner which produces approximately 30 nm particles. Briefly, the two solutions are heated separately to 90° C. The reducing solution is added to the gold solution while vigorously stirring. The combined solution is boiled (100° C.) for at least 10 minutes.

Affinity purified goat anti-fibronectin antibody (prepared as described in Example 4) was bound to the colloidal gold by adsorption. Briefly, the collodial gold solution prepared above was combined with the antibody (5-10 μg/mL) in water. Following conjugation, the conjugate solution was stabilized by the addition of 5% BSA and 5% polyvinylpyrrolidine (final concentration).

The stock conjugate was concentrated approximately 10- to 12-fold by ultrafiltration using a hollow fiber filter. The concentrated conjugate was diluted to an appropriate level in 15 mM Tris, 2% BSA, 0.1% Tween 20, 0.2% polyethylene glycol, 8% polyvinylpyrrolidine and 0.04% thimerosal. An appropriate concentration was determined by using a range of dilutions in a sample assay procedure as described below and determining the dilution which produces the best result.

The selected conjugate dilution is placed in polyethylene sample collection tubes and lyophilized. The tubes are fitted with 2μ pore size polyethylene sample filters (Porex Technologies, Fairburn, Ga.) during the lyophilization process. The lyophilized conjugate is individually packaged in a foil pouch with desiccant.

The conjugate reconstitution buffer is 100 mM sodium acetate. This buffer is packaged as a unit dose in a 1 ml disposable tube.

The wash solution is water packaged as a unit dose in a disposable tube.

The kit additionally contains an individually packaged sterile dacron swab and a procedural summary card.

The assay was performed as follows.
1. Before collecting the sample, remove the plastic tube containing gold conjugate from the foil pouch, remove the dropper tip and add the entire contents of the tube containing the conjugate reconstitution buffer.
2. Collect the sample with the swab provided. During a sterile speculum examination, insert the swab into the posterior fornix of the vagina, twirl for approximately 10 seconds to absorb fluid. Immediately proceed to perform the test. Samples may not be stored for later testing. Place the swab in the gold conjugate solution and mix rapidly with an up and down motion for 10 to 15 seconds.
3. Remove as much liquid as possible from the swab by rolling the tip on the inside of the tube. Dispose of the swab in a manner consistent with handling potentially infectious materials.
4. Replace the dropper tip on the plastic tube and immediately dispense the entire volume of diluted filtered sample onto the surface of the membrane device.
5. After the sample liquid has been absorbed into the membrane surface, add a few drops of wash solution and observe the results.
6. A negative result is indicated by a red color in the procedural control area of the membrane only. A positive result is indicated by a pink or red spot in the test zone of the membrane as well as in the control zone.

I claim:

1. A kit for detecting fetal fibronectin in a vaginal sample comprising:
   a. an anti-(fetal fibronectin) antibody;
   b. an anti-fibronectin antibody,
      wherein either said anti-(fetal fibronectin) antibody or said anti-fibronectin antibody is adhered to an insoluble support; and
   c. a device selected from the group consisting of a vaginal sample collection device, a vaginal sample filtration device, and a vessel containing a vaginal sample diluent.

2. The kit of claim 1 wherein said anti-(fetal fibronectin) antibody is a monoclonal antibody.

3. The kit of claim 2 wherein said anti-(fetal fibronectin) antibody is FDC-6.

4. The kit of claim 1 wherein said anti-fibronectin antibody is a polyclonal antibody.

5. The kit of claim 4 wherein said anti-fibronectin antibody is labeled.

6. The kit of claim 5 wherein said label is an enzyme.

7. The kit of claim 6 wherein said enzyme is alkaline phosphatase.

8. The kit of claim 7 wherein said kit additionally comprises enzyme substrate.

9. The kit of claim 8 wherein said enzyme substrate is phenolphthalein monophosphate.

10. The kit of claim 5 wherein said label is colloidal gold.

11. The kit of claim 1 wherein said insoluble support comprises a microtiter plate or a strip of wells of a microtiter plate.

12. The kit of claim 11 wherein said kit additionally comprises a microtiter plate cover.

13. The kit of claim 11 wherein said kit includes a strip of wells of a microtiter plate and additionally comprises a holder for said strip.

14. The kit of claim 1 wherein said kit additionally comprises a positive, control.

15. The kit of claim 14 wherein said positive control is amniotic fluid of a known fetal fibronectin concentration.

16. The kit of claim 15 wherein said fetal fibronectin concentration is from about 10 to about 100 ng/mL.

17. The kit of claim 16 wherein said amniotic fluid is diluted in 0.05M Tris buffer pH 7.4, 1% bovine serum albumin, 0.15M sodium chloride, 0.02% Sodium Azide, 5 mM ethylenediamine tetraacetic acid, 1 mM phenylmethylsulfonyl fluoride, and 500 Kallikrein Units/ml of Aprotinin.

18. The kit of claim 1 wherein said kit additionally comprises a negative control.

19. The kit of claim 18 wherein said negative control is 0.05M Tris buffer pH 7.4, 1% bovine serum albumin, 0.15M sodium chloride, 0.02% Sodium Azide, 5 mM ethylenediamine tetraacetic acid, 1 mM phenylmethylsulfonyl fluoride, and 500 Kallikrein Units/ml of Aprotinin.

20. The kit of claim 1 wherein said kit additionally comprises at least one sample filtering device.

21. The kit of claim 20 wherein said sample filtering device dispenses a predetermined volume of filtered sample.

22. The kit of claim 1 wherein said kit additionally comprises a rinse buffer.

23. The kit of claim 22 wherein said rinse buffer is 0.02M Tris, 0.08M sodium chloride and 0.05% Tween-20.

24. The kit of claim 23 wherein said rinse buffer additionally comprises sodium azide.

25. The kit of claim 23 wherein said rinse solution is packaged in concentrated form.

26. The kit of claim 1 wherein said unsoluble support is a membrane.

27. The kit of claim 26 wherein said membrane is nylon.

28. The kit of claim 26 wherein said membrane is placed over an absorbent layer.

29. The kit of claim 28 wherein a flow control layer is intermediate said membrane and said absorbent layer.

30. The kit of claim 26 wherein said kit additionally comprises a sample filtering device which contains labeled anti-fibronectin antibody.

31. The kit of claim 7 wherein the alkaline phosphatase-labeled anti-fibronectin antibody is in an enzyme conjugate buffer comprising 50 mM Tris, pH 7.2; 2% D-Sorbitol; 2% bovine serum albumin; 0.01% Tween-20; 1 mM $MgCl_2$; 0.1% $ZnCl_2$; and optionally 0.1% sodium azide.

32. The kit of claim 9 wherein the phenolphthalein monophosphate is in an enzyme substrate solution containing 2-amino-2-methyl-1-propanol and $MgCl_2$.

33. The kit of claim 32 wherein said enzyme substrate solution comprises 1 mg/ml phenolphthalein monophosphate; 0.4M 2-amino-2-methyl-1-propanol, pH 10; 0.1 mM $MgCl_2$; and, optionally 0.2% sodium azide.

34. The kit of claim 10 wherein the gold-labeled anti-fibronectin antibody conjugate is in a protein matrix in a conjugate buffer comprising 15 mM Tris; 0.1% Tween 20; 0.2% polyethylene glycol; 8% polyvinylpyrrolidine; and, optionally 0.04% thimerosal.

35. The kit of claim 34 wherein the protein matrix comprises 2% bovine serum albumin.

36. The kit of claim 35 wherein said antibody conjugate is lyophilized.

37. The kit of claim 36 wherein said kit includes a conjugate reconstitution buffer.

38. The kit of claim 37 wherein said conjugate reconstitution buffer comprises 100 mM sodium acetate.

39. The kit of claim 1 wherein said device is a vaginal sample collection device.

40. The kit of claim 1 wherein said device comprises a swab.

41. The kit of claim 40 wherein said swab is a dacron swab.

42. A kit for detecting a fetal fibronectin in a vaginal sample comprising:
  a. an anti-(fetal fibronectin) antibody adhered to a well of a microtiter plate;
  b. an alkaline phosphatase-labeled anti-fibronectin antibody in an enzyme conjugate buffer comprising 50 mM Tris, pH 7.2; 2% D-Sorbitol; 2% bovine serum albumin; 0.01% Tween-20; 1 mM $MgCl_2$; 0.1% $ZnCl_2$; and optionally 0.1% sodium azide;
  c. phenolphthalein monophosphate is in a enzyme substrate solution comprising 1 mg/ml phenolphthalein monophosphate; 0.4M 2-amino-2-methyl-1-propanol, pH 10; 0.1 mM $MgCl_2$; and, optionally 0.2% sodium azide; and
  d. a device selected from the group consisting of a vaginal sample collection device, a vaginal sample filtration device, and a vessel containing a vaginal sample diluent.

43. The kit of claim 42 wherein the kit additionally contains a rinse buffer concentrate comprising 0.1M Tris, pH 7.4; 4.0M NaCl; 2.5% Tween-20; and, optionally 1.0% sodium azide.

44. The kit of claim 42 wherein the kit additionally comprises a positive and a negative control.

45. A kit for detecting a fetal fibronectin in a test sample comprising:
  a. an anti-(fetal fibronectin) antibody adhered to a nylon membrane, said membrane placed over an absorbent layer and having a flow control layer intermediate said membrane and said absorbent layer;
  b. a lyophilized gold-labeled anti-fibronectin antibody conjugate comprising 15 mM Tris; 2% bovine serum albumin; 0.1% Tween 20; 0.2% polyethylene glycol; 8% polyvinylpyrrolidine; and, optionally 0.04% thimerosal; and c. a reconstitution buffer comprising 100 mM sodium acetate.

46. The kit of claim 45 wherein said membrane additionally includes a control region comprising membrane-affixed fibronectin.

* * * * *

UNITED STATES PATENT AND TRADEMARK OFFICE
CERTIFICATE OF CORRECTION

PATENT NO. : 5,281,522

DATED : January 25, 1994

INVENTOR(S) : Andrew E. Senyei and Nelson N. H. Teng

It is certified that error appears in the above-indentified patent and that said Letters Patent is hereby corrected as shown below:

Column 7, line 57:
Delete "unlabele" and insert --unlabeled--

Column 33, line 61:
Delete "unsoluble" and insert --insoluble--

Signed and Sealed this

Eighteenth Day of October, 1994

Attest:

BRUCE LEHMAN

Attesting Officer     Commissioner of Patents and Trademarks